(12) United States Patent
Hoeffkes et al.

(10) Patent No.: US 7,060,109 B2
(45) Date of Patent: Jun. 13, 2006

(54) HAIR DYEING AGENTS CONTAINING INDIGO DERIVATIVES

(75) Inventors: Horst Hoeffkes, Duesseldorf (DE); Karin Nelles, Monheim (DE); Hinrich Moeller, Monheim (DE)

(73) Assignee: Henkel Kommanditgesellschaft auf Aktien (Henkel KGa A), Duesseldorf (DE)

( * ) Notice: Subject to any disclaimer, the term of this patent is extended or adjusted under 35 U.S.C. 154(b) by 421 days.

(21) Appl. No.: 10/380,343

(22) PCT Filed: Sep. 11, 2001

(86) PCT No.: PCT/EP01/10480

§ 371 (c)(1), (2), (4) Date: Mar. 12, 2003

(87) PCT Pub. No.: WO02/22092

PCT Pub. Date: Mar. 21, 2002

(65) Prior Publication Data

US 2004/0031108 A1 Feb. 19, 2004

(30) Foreign Application Priority Data

Sep. 14, 2000 (DE) ................. 100 45 856

(51) Int. Cl.
*A61K 7/13* (2006.01)

(52) U.S. Cl. ................. 8/405; 8/574; 8/575; 8/576; 8/577; 8/607; 8/608; 548/364.7; 549/469

(58) Field of Classification Search ............... 8/405, 8/575, 576, 607, 608, 574, 577; 548/364.7; 549/469

See application file for complete search history.

(56) References Cited

U.S. PATENT DOCUMENTS

| | | | |
|---|---|---|---|
| 4,003,699 A | 1/1977 | Rose et al. ............. 8/102 |
| 4,865,774 A | 9/1989 | Fabry et al. ............. 252/554 |
| 4,931,218 A | 6/1990 | Schenker et al. ........... 252/551 |
| 5,061,289 A | 10/1991 | Clausen et al. ............. 8/409 |
| 5,199,954 A | 4/1993 | Schultz et al. ............. 8/408 |
| 5,294,726 A | 3/1994 | Behler et al. ............. 884/98 |
| 5,380,340 A | 1/1995 | Neunhoeffer et al. .......... 8/409 |
| 5,534,267 A | 7/1996 | Neunhoeffer et al. ....... 424/701 |
| 5,663,366 A | 9/1997 | Neunhoeffer et al. .... 508/371.4 |
| 5,743,919 A | 4/1998 | Moeller et al. ............. 8/409 |
| 5,766,576 A | 6/1998 | Lowe et al. ............. 424/407 |
| 5,769,903 A * | 6/1998 | Audousset et al. ........... 8/409 |
| 5,879,412 A * | 3/1999 | Rondeau et al. .............. 8/411 |
| 6,099,592 A | 8/2000 | Vidal et al. ............. 8/409 |
| 6,284,003 B1 | 9/2001 | Rose et al. ............. 8/412 |
| 6,371,993 B1 | 4/2002 | Moeller et al. ............. 8/407 |

FOREIGN PATENT DOCUMENTS

| | | |
|---|---|---|
| DE | 23 59 399 A1 | 6/1975 |
| DE | 197 45 354 A1 | 1/1989 |
| DE | 37 35 030 A1 | 2/1989 |
| DE | 38 43 892 A1 | 6/1990 |
| DE | 39 26 344 A1 | 2/1991 |
| DE | 41 33 957 A1 | 4/1993 |
| DE | 43 35 627 A1 | 4/1995 |
| DE | 44 09 143 A1 | 9/1995 |
| DE | 195 43 988 A1 | 5/1997 |
| DE | 196 30 274 A1 | 1/1998 |
| DE | 196 30 275 A1 | 1/1998 |
| DE | 196 48 020 C1 | 3/1998 |
| DE | 197 17 223 A1 | 10/1998 |
| DE | 197 17 224 A1 | 10/1998 |
| DE | 197 17 280 A1 | 10/1998 |
| DE | 37 23 354 A1 | 4/1999 |
| DE | 197 45 356 A1 | 4/1999 |
| EP | 359 465 A2 A3 | 3/1990 |
| EP | 0 530 229 B1 | 6/1995 |
| EP | 0 740 931 B1 | 8/1997 |
| FR | 2 787 708 A1 | 6/2000 |
| FR | 2787708 A1 * | 6/2000 |
| GB | 1 026 978 | 4/1966 |
| GB | 1 153 196 | 5/1969 |
| JP | 02019576 | 1/1990 |
| WO | WO 94/08969 A1 | 4/1994 |
| WO | WO 94/08970 A1 | 4/1994 |
| WO | WO 96/15765 A1 | 5/1996 |

OTHER PUBLICATIONS

The Science of Hair Care, Chapter 7, pp. 235-261, published in vol. 7, Dermatology, Marcel Dekker Inc. NY/Basle (1986).

(Continued)

*Primary Examiner*—Eisa Elhilo
(74) *Attorney, Agent, or Firm*—Stephen D. Harper; Gregory M. Hill

(57) ABSTRACT

Compositions and method for coloring keratin fibers consisting of derivatives of benzo[b]furan-3-one and/or benzo-[b]-thiophen-3-one compounds with special reactive components. These compositions form intensely colored compounds when applied to keratin fibers. The compositions may also be used with substantive dyes and/or oxidation colorants.

11 Claims, No Drawings

OTHER PUBLICATIONS

The Science of Hair Care, Chapter 8, pp. 263-286, published in vol. 7, Dermatology, Marcel Dekker Inc. NY/Basle (1986).

K. Schrader, Grudlagen un Rezepturen der Kosmetika [Bases and Formulations Cosmetics], 2 nd Edition, Huethig Buch Verlag, Heidelberg, Germany (1989).

A. Pawlick, Dissertation, Tech. Universitat Braunschweig, pp. 98-101 (1995).

J. Szabo et al., Acta Chim. Acad. Sci. Hung. vol. 17, pp. 201-209 (1958).

M. C. Kloetel et al., J. Org. Chem. vol. 20, pp. 38-49 (1955).

* cited by examiner

HAIR DYEING AGENTS CONTAINING INDIGO DERIVATIVES

CROSS REFERENCE TO RELATED APPLICATIONS

This application is a national stage application under 35 USC 371 of international application PCT/EP01/10480 filed on Sep. 11, 2001, the international application not being published in English. This application also claims priority under 35 USC 119 to DE 100 45 856.4 filed on Sep. 14, 2000.

BACKGROUND OF THE INVENTION

This invention relates to compositions for coloring keratin fibers which contain special derivatives of benzo[b]furan-3-one and/or benzo-[b]-thiophen-3-one and reactive compounds, to a coloring process using this dye precursor combination and to the use of this combination for coloring keratin fibers.

Nowadays, human hair is treated in many different ways with hair-care preparations. Such treatments include, for example, the cleaning of hair with shampoos, the care and regeneration of hair with rinses and treatments and the bleaching, coloring and shaping of hair with coloring and tinting formulations, wave formulations and styling preparations. Among these, formulations for modifying or shading the color of the hair occupy a prominent position.

Colorants or tints containing substantive dyes as their coloring component are normally used for temporary colors. Substantive dyes are based on dye molecules which are directly absorbed onto the hair and do not require an oxidative process for developing the color. Dyes such as these include, for example, henna which has been used since ancient times for coloring the body and hair. Corresponding colors are generally sensitive to shampooing so that an often unwanted change of shade or even a visible "decoloration" can occur.

So-called oxidation colorants are used for permanent, intensive colors with corresponding fastness properties. Oxidation colorants normally contain oxidation dye precursors, so-called primary intermediates and secondary intermediates. The primary intermediates form the actual dyes with one another or by coupling with one or more secondary intermediates under the influence of oxidizing agents or atmospheric oxygen. Oxidation colorants are distinguished by excellent long-lasting coloring results. Natural-looking colors normally require a mixture of a relatively large number of oxidation dye precursors; in many cases, substantive dyes are used for shading.

Finally, a new coloring process has very recently attracted considerable attention. In this process, precursors of the natural hair dye melanin are applied to the hair. These precursors then form "nature-analogous" dyes in the course of oxidative processes. One such process using 5,6-dihydroxyindoline as the dye precursor is described in EP-B1-530 229. Another new coloring system is described, for example, in EP-A2-359 465. In this process, selected isatin derivatives are reacted with aromatic amines in the coloring of keratin fibers.

Nevertheless, there is always an ongoing search for other coloring systems which give intensive colors of the fibers with excellent fastness properties.

SUMMARY OF THE INVENTION

It has now surprisingly been found that special derivatives of benzo[b]furan-3-one and/or benzo[b]thiophen-3-one react with special reactive components to form intensively colored compounds which are capable of coloring keratinous fibers.

DETAILED DESCRIPTION OF THE INVENTION

In a first embodiment, therefore, the present invention relates to a composition for coloring keratinous fibers which contains as dye precursors in a cosmetically acceptable medium (a) at least one derivative of benzo[b]furan-3-one and/or at least one derivative of benzo[b]thiophen-3-one corresponding to formula (1):

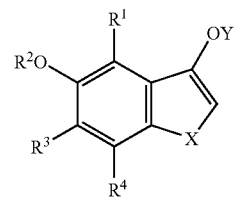

in which
X is sulfur or oxygen,
Y is hydrogen, a $C_{1-4}$ alkyl group or a $C_{1-4}$ acyl group,
the substituents $R^1$, $R^3$ and $R^4$ independently of one another represent
  hydrogen,
  a $C_{1-4}$ alkyl group which may optionally be substituted by
    one or more hydroxy group(s)
    an optionally substituted amino group,
    a carboxy group optionally esterified with a $C_{1-4}$ alkyl group or
    a group —$SO_2R^5$, where $R^5$ is a hydroxy group, an optionally substituted amino group or a $C_{1-4}$ alkyl group,
  an optionally substituted amino group,
  a perfluorinated $C_{1-4}$ alkyl group,
  a cyano group,
  a $C_{2-5}$ alkenyl group,
  a nitro group,
  a halogen atom,
  an optionally $C_{1-4}$-alkyl-substituted mercapto group,
  a group —$SO_2R^5$ or
  a group —$OR^6$,
  an optionally esterified or amidated carboxyl group and
$R^2$ and optionally $R^6$ independently of one another represent
  hydrogen,
  a $C_{1-4}$ alkyl group which may optionally be substituted by
    one or more hydroxy group(s),
    an optionally substituted amino group,
    a carboxy group optionally esterified with a $C_{1-4}$ alkyl group or
    a group —$SO_2R^5$, or
  a perfluorinated $C_{1-4}$ alkyl group, and (b) at least one reactive compound selected from
  (b1) reactive carbonyl compounds selected from the group of aromatic, heteroaromatic or unsaturated aldehydes or ketones, dialdehydes or diketones or acetals, semiaminals or imine derivatives of such reactive carbonyl compounds and/or
  (b2) CH-active compounds corresponding to formula (2) or (3):

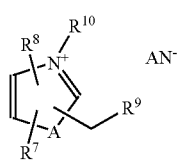

(2)

in which $R^{10}$ is a $C_{1-10}$ alkyl group, a $C_{2-4}$ alkenyl group, a $C_{2-4}$ hydroxyalkyl group, a $C_{2-4}$ carboxyalkyl group, a $C_{2-4}$ sulfoalkyl group or an aralkyl group, $R^7$ and $R^8$ independently of one another represent a hydrogen atom, a $C_{1-4}$ alkyl group, a halogen atom, a hydroxy group, a $C_{1-4}$ alkoxy group or a nitro group or together form a fused aromatic ring, $R^9$ is a hydrogen atom, a $C_{1-4}$ alkyl group or an aryl group, A is an oxygen or a sulfur atom, the group —CH═CH— or >N—$R^{11}$, where $R^{11}$ is a $C_{1-4}$ alkyl group, a $C_{2-4}$ carboxyalkyl group, a $C_{2-4}$ sulfoalkyl group, a $C_{2-4}$ sulfoxyalkyl group, a $C_{2-4}$ hydroxyalkyl group or an aralkyl group, and AN⁻ is an anion selected from halide, $C_{1-4}$ alkyl sulfate, $C_{1-4}$ alkanesulfonate, arenesulfonate, $C_{1-4}$ perfluoroalkane-sulfonate, tetrafluoroborate, perhalogenate, sulfate, hydrogen sulfate or carboxylate,

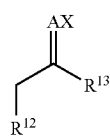

(3)

in which $R^{12}$ is a $C_{1-4}$ acyl group, a $C_{1-4}$ alkylsulfonyl group, a $C_{1-4}$ alkylsulfinyl group, a $C_{1-4}$ alkylamino group, a di-$C_{1-4}$-alkyamino group, a vinyl carbonyl group, a methineimino group, a nitrile group, an ester or carboxylic acid amide group which may optionally be substituted by a $C_{1-4}$ alkyl group, a $C_{2-4}$ hydroxyalkyl group or an aryl group, and $R^{13}$ represents a $C_{1-4}$ acyl group, a $C_{1-4}$ alkoxy group, a $C_{1-4}$ alkylamino group, a $C_{1-4}$ acylamino group or a di-$C_{1-4}$-alkylamino group; the substituents $R^{12}$ and $R^{13}$ together with the rest of the molecule may also form a 5-, 6- or 7-membered ring system from the series of thiazolidine-2,5-diones, thiazolidine-2-thion-5-ones, perhydropyrimidine-2,4,6-triones, perhydropyrimidine-2-thione-4,6-diones, cyclopentane-1,3-diones, cyclohexane-1,3-diones, indane-1,3-diones, 2-pyrazoline-5-ones, 1,2-dihydro-6-hydroxy-2-hydroxypyridines or enol esters thereof, and AX represents oxygen, sulfur or a dicyanomethylene group.

Keratinous fibers in the context of the present invention are understood to be pelts, wool, feathers and, in particular, human hair.

Examples of the $C_{1-4}$ alkyl groups mentioned as substituents in the compounds according to the invention are the groups methyl, ethyl, propyl, isopropyl and butyl. Ethyl and methyl are preferred alkyl groups. Preferred $C_{1-4}$ hydroxyalkyl groups are the groups hydroxymethyl, 2-hydroxyethyl, 3-hydroxypropyl or 4-hydroxybutyl; 2-hydroxyethyl is a particularly preferred hydroxyalkyl group. According to the invention, the other terms used are derived from the definitions given here. According to the invention, a particularly preferred perfluorinated $C_{1-4}$ alkyl group is the trifluoromethyl group. According to the invention, a particularly preferred carboxy-$C_{1-4}$-alkyl group is the carboxymethyl group. According to the invention, examples of a halogen atom are an F, a Cl or a Br atom. A Cl atom is particularly preferred. Preferred amino-$C_{1-4}$-alkyl groups are the aminomethyl, aminoethyl, diethylaminomethyl and dimethylaminomethyl groups. Preferred substituted amino groups are the amino-$C_{1-4}$-alkylamino groups, among which the aminoethylamino group is particularly preferred. A preferred acyl group is the acetyl group. Preferred alkenyl groups are the vinyl group and the allyl group.

According to the invention, compounds of formula (1) in which the substituent Y is hydrogen are particularly preferred. In the case of these compounds, which are present in a keto-enol equilibrium in accordance with formula (1a):

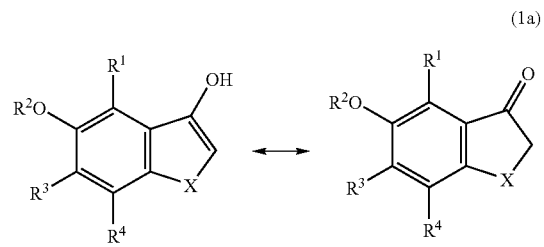

(1a)

all statements in the present specification apply both to the keto form of these compounds and to the enol form.

Compounds of formula (1) where $R^1$ and/or $R^4$ are hydrogen have proved to be particularly advantageous.

Other preferred compounds of formula (1) can be those where at least one of the substituents $R^1$, $R^3$ or $R^4$ is not hydrogen.

In a particularly preferred embodiment, the substituent —$OR^2$ is selected from a hydroxy group, a methoxy group, a carboxymethyl group and a 2-hydroxyethoxy group.

In a first variant of the present invention, preferred compounds of formula (1) are those where X is an oxygen atom such as, for example, the compounds 5-carboxymethoxy benzo[b]furan-3-one, 5-hydroxybenzo[b]furan-3-one or 5-(2'-hydroxyethoxy)-benzo[b]furan-3-one.

In a second variant of the present invention, preferred compounds are those where X is a sulfur atom such as, for example, the compounds 5-hydroxybenzo[b]thiophen-3-one, 5-carboxymethoxybenzo[b]thiophen-3-one, 5,6-dihydroxybenzo[b]thiophen-3-one or 6-hydroxy-5-methoxybenzo[b]thiophen-3-one.

Particularly preferred compositions according to the invention contain at least one compound corresponding to formula (1) and at least one reactive carbonyl compound selected from the group of aromatic, heteroaromatic or unsaturated aldehydes or ketones, the dialdehydes or diketones or the acetals, semiaminals or imine derivatives of such reactive carbonyl compounds.

Suitable reactive carbonyl compounds of the aromatic aldehyde type are described, for example, in German patent applications DE 196 30 274 A1 and DE 196 30 275 A1. Other suitable arylaldehydes are known from U.S. Pat. No. 5,199,954. According to the invention, particularly suitable compounds are:

benzaldehyde and benzaldehyde derivatives thereof such, as for example, 2-hydroxybenzaldehyde, 4-hydroxy-3-methoxybenzaldehyde (vanillin), 3-hydroxy-4-methoxybenzaldehyde (isovanillin), 3,4-dihydroxybenzaldehyde, 4-hydroxybenzaldehyde, 3,5-dimethoxy-4-hydroxybenzaldehyde, 4-dimethylaminobenzaldehyde, 4-hydroxy-2-methoxybenzaldehyde, 3,5-dimethyl-4-hydroxybenzaldehyde, 4-dimethylamino-2-methoxybenzaldehyde, 2-hydroxy-3-methoxybenzaldehyde, 2,4-dihydroxybenzaldehyde, 3,4-dihydroxybenzaidehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxybenzaldehyde, 2,5-dimethoxybenzaldehyde, 3,5-dimethoxybenzaldehyde, 3,4-dimethoxybenzaldehyde, 4-ethoxybenzaldehyde, 4-carboxybenzaldehyde, 4-diethylamino-3-methoxybenzaldehyde, 4-diethylamino-2-hydroxybenzaldehyde, 4-dibutylaminobenzaldehyde, 3,4-dimethoxy-5-hydroxybenzaldehyde, 3-ethoxy-4-hydroxybenzaldehyde, biphenyl-4-carbaldehyde, 2-nitrobenzaldehyde, 3-nitrobenzaldehyde und 4-nitrobenzaldehyde, 1-naphthaldehyde and derivatives thereof such as, for example, 4-hydroxy-1-naphthaldehyde, 4-methoxy-1-naphthaldehyde, 4-dimethylamino-1-naphthaldehyde and 2-methoxy-1-naphthaldehyde and cinnamaldehyde and derivatives thereof such as, for example, 4-hydroxy-3-methoxycinnamaldehyde (coniferyl aldehyde), 4-dimethylaminocinnamaldehyde and 3,5-dimethoxy-4-hydroxy-cinnamaldehyde.

Derivatives of the aromatic aldehydes which carry an optionally substituted hydroxy or amino group in the para position to the substituent bearing the aldehyde function are particularly preferred. The free hydroxy group and the di-($C_{1-4}$-alkyl)-amino group, for example the dimethylamino group, is particularly preferred.

Suitable reactive carbonyl compounds of the heteroaromatic aldehyde type are described, for example, in German patent application DE 197 172 806. Particularly suitable dyes are, for example, trans-β-(2-furyl)-acrolein, 1-methylindole-3-carbaldehyde, 2-(1,3,3-trimethyl-2-indolinylidene)-acetaldehyde, 4-methylimidazole-5-carbaldehyde, 3-methoxy-4-(1-pyrrolidinyl)-benzaldehyde, pyrrole-2-carbaldehyde, thiophene-2-carbaldehyde, thiophene-3-carbaldehyde, chromone-3-carbaldehyde, 6-methylchromone-3-carbaldehyde, N-methylpyrrole-2-carbaldehyde, 5-methylfurfural, 6-hydroxychromene-3-carbaldehyde, N-ethylcarbazole-3-carbaldehyde, indole-3-carbaldehyde, 6-methylindole-3-carbaidehyde, thiophene-2,3-dicarbaldehyde, thiophene-2,5-dicarbaldehyde oder antipyrine-4-carbaldehyde. Special products of this type containing a pyridinium group are described in German patent application DE 197 45 356, for example the eminently suitable 4-formyl-1-methylpyridinium benzenesulfonate and 4-formyl-1-methylquinolinium methanesulfonate or methylsulfate or p-toluenesulfonate and 2-formyl-1-methylquinolinium-p-toluenesulfonate hydrate.

Suitable reactive carbonyl compounds of the unsaturated aldehyde type are described, for example, in German patent application DE 197 17 224. Glutaconaidehyde in the form of its salts, for example its alkali metal or tetrabutyl ammonium salt, or 2-chloro-3-hydroxymethylene-1-cyclohexene-1-carbaldehyde is particularly suitable for the purposes of the present invention. Another aldehyde suitable for the purposes of the invention is 5-(4-diethylamino)-phenyl)-2,4-pentadienal.

Dialdehydes and diketones and derivatives thereof which are suitable as reactive carbonyl compounds for the purposes of the invention are, for example, alicyclic and cyclic 1,2-, 1,3- or 1,4-dicarbonyl compounds, such as isatin, 1-H-quinoline-2,3,4-trione, ninhydrin, alloxan, isobarbituric acid, benzene-1,4-dicarbaldehyde, 1,2-phthaldialdehyde, 1,2-cyclohexanedione, 1,3-cylcohexanedione, 1,4-cyclohexanedione, dimedone, 1,2-cyclopentadione, 1,3-cyclopentadione, p- and o-quinones, 2-methyl-1,4-naphthoquinone, 1,3-indanediones and derivatives thereof. Such dyes can be found, for example, in German Offenlegungsschrift DE 43 35 627 A1. Suitable compounds are, for example, malondialdehyde, preferably in the form of its dimethylacetal, 1,3-indanedione or 2-acetyl-1,3-cyclohexanedione. Another suitable 1,2-dicarbonyl compound is the potassium salt of isatic acid.

Diketones suitable in accordance with the invention as a reactive carbonyl compound also include cyclic dicarbonyl compounds such as, for example, the isatin and isatin derivatives described, for example, in German Offenlegungsschrift DE 44 09 143 A1. According to the invention, isatin, isatin-5-sulfonic acid potassium salt, N-allyl isatin, 1-piperidinomethyl isatin, 1-hydroxymethyl isatin and 1-diethylaminomethyl isatin are preferred.

Another cyclic dicarbonyl compound suitable as a reactive carbonyl compound is, for example, dehydroascorbic acid of which the suitability as a hair dye is known from German patent application DE 197 45 354.

Finally, acetals, imine derivatives and semiaminals of the reactive carbonyl compounds mentioned are also suitable for the purposes of the invention. Such compounds are obtained by reaction of the carboxyl group with primary alcohols or amines and optionally elimination of water.

The group of merocyanine and cyanine or azomethine dyes are obtainable from the unsaturated dialdehydes and diketones. Suitable imine derivatives of gutacondialdehyde are, for example, the mono-N-methylaniline derivative of glutaconaldehyde (5-N-methylanilinopentadienal) or N-(5-anilino-2,4-pentadien-1-ylidene)-anilinium chloride. Another suitable vinylogous cyanine dye is 7-dimethylamino-2,4,6-heptatrienylidene dimethyl ammonium perchlorate. Such compounds are known as hair colorant components, for example from German patent application DE 197 17 223.

The following are mentioned as examples of preferred compounds of formula (2): 1,4-dimethylquinolinium, 1,2-dimethylquinolinium, 1,4-dimethylpyridinium, 1,2-dimethylpyridinium, 2,4,6-trimethylpyrilium, 2-methyl-1-ethylquinolinium, 2,3-dimethylisoquinolinium, 1,2,3,3-tetramethyl-3H-indolium, 2,3-dimethylbenzothiazolium, 2,3-dimethyl-6-nitrobenzothiazolium, 3-benzyl-2-benzothiazolium, 2-methyl-3-propylbenzothiazolium, 2,4-dimethyl-3-ethylthiazolium, 3-(2-carboxyethyl)-2,5-dimethylbenzothiazolium, 1,2,3-trimethylbenzimidazolium, 5,6-dichloro-1,3-diethyl-2-methylbenzimidazolium, 3-ethyl-2-methylbenzothiazolium, 3-ethyl-2-methylnaphtho[1,2-d]thiazolium, 5-chloro-3-ethyl-2-methylbenzothiazolium, 3-ethyl-2-methylbenzoxazolium salts which may be present, for example as chlorides, bromides, iodides, methanesulfonates, benzenesulfonates, p-toluenesulfonates, trifluoromethanesulfonates, methylsulfates, tetrafluororborates and 2-methyl-3-(3-sulfopropyl)-benzothiazolium hydroxide (inner salt), 4-methyl-1-(3-sulfopropyl)-pyridinium hydroxide (inner salt, 4-methyl-1-(3-sulfopropyl)-quinolinium hydroxide (inner salt), 5-methoxy-2-methyl-3-(3-sulfopropyl)-benzothiazolium hydroxide (inner salt) and mixtures of the above.

According to the invention, the compounds of formula (2) may also be present in the form of their bases or the enamines, depending on the pH of the particular composition.

Examples of compounds corresponding to formula (3) are rhodamine, rhodamine-3-acetic acid, barbituric acid, thiobarbituric acid, 1,3-dimethyl and 1,3-diethyl thiobarbituric acid, oxindole, 3-indoxyl acetate, coumaranone, 1-methyl-3-phenylpyrazolinone, indane-1,3-dione, cyclopentane-1,3-dione, 1,2-dihydro-1-ethyl-6-hydroxy-4-methyl-2-oxo-3-pyridine carbonitrile, 1-dicyanomethylene indane and mixtures of the above.

The variety of shades obtainable with the coloring system according to the invention can be further increased by combination with one or more compounds containing a primary or secondary amino or hydroxy group selected from the group of amino acids and peptides, aromatic amines, phenols, aminophenols and nitrogen-containing heterocycles. In many cases, darker shades are also obtained.

Suitable amino acids are, in particular, the naturally occurring and synthetic amino acids, for example arginine, histidine, phenylalanine, dihydroxy phenylalanine, ornithine, lysine. Suitable peptides are, above all, oligo- and polypeptides which have sufficient solubility in water for use in the preparations according to the invention for reducing keratin. Examples include glutathione and the oligopeptides present in the hydrolyzates of collagen, keratin, elastin, casein or vegetable proteins, such as soya protein, wheat protein, algal protein or almond protein.

Suitable aromatic amines and aminophenols are N,N-dimethyl-, N,N-diethyl-, N-(2'-hydroxyethyl)-N-ethyl-, N,N-bis-(2'-hydroxyethyl)-, N-(2'-methoxyethyl)-, 2-chloro-, 2,3-, 2,4- and 2,5-dichloro-p-phenylenediamine, 2,5-dihydroxy-4-morpholinoaniline dihydrobromide, 2-, 3- and 4-aminophenol, 2-aminomethyl-4-aminophenol, 2-hydroxymethyl-4-aminophenol, o- and p-phenylenediamine, o- and m-toluylenediamine, 2,5-diaminophenol, -toluene and -phenethol, 4-amino-3-methylphenol, 2-(2',5'-diaminophenyl)-ethanol, 2,4-diaminophenoxyethanol, 2-(2',5'-diaminophenoxy)-ethanol, 4-methylamino-, 3-amino-4-(2'-hydroxyethyloxy)-, 3,4-methylenediamino- and 3,4-methylenedioxyaniline, 3-amino-2,4-dichloro-, 4-methylamino-, 2-methyl-5-amino-, 3-methyl-4-amino-, 2-methyl-5-(2'-hydroxyethylamino)-, 6-methyl-3-amino-2-chloro-, 2-methyl-5-amino-4-chloro-, 3,4-methylenedioxy-, 5-(2'-hydroxyethylamino)-4-methoxy-2-methylphenol, 4-amino-2-hydroxymethylphenol, 1,3-diamino-2,4-dimethoxybenzene, 2-, 3-, 4-aminobenzoic acid, -phenylacetic acid, 2,3-, 2,4-, 2,5-, 3,4-, 3,5-diaminobenzoic acid, 4-, 5-aminosalicylic acid, 3-amino-4-hydroxy-, 4-amino-3-hydroxybenzoic acid, 2-, 3-, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-, 1,2,4-triaminobenzene, 1,2,4,5-tetraminobenzene, 2,4,5-triaminophenol, pentaminobenzene, hexaminobenzene, 2,4,6-triaminoresorcinol, 4,5-diaminopyrocatechol, 4,6-diaminopyrogallol, 3,5-diamino-4-hydroxypyrocatechol, aromatic anilines and phenols containing another aromatic radical corresponding to formula (4):

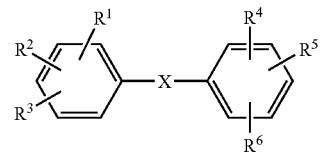

in which $R^1$ is a hydroxy group or an amino group which may be substituted by $C_{1-4}$ alkyl, $C_{1-4}$ hydroxyalkyl or $C_{1-4}$-alkoxy-$C_{1-4}$-alkyl groups, $R^2$, $R^3$, $R^4$, $R^5$ and $R^6$ represent hydrogen, a hydroxy group or an amino group, which may be substituted by $C_{1-4}$ alkyl, $C_{1-4}$ hydroxyalkyl, $C_{1-4}$ aminoalkyl or $C_{1-4}$-alkoxy-$C_{1-4}$-alkyl groups, a carboxylic or sulfonic acid group and X is a direct bond, a saturated or unsaturated, optionally hydroxy-substituted carbon chain containing 1 to 4 carbon atoms, a carbonyl, sulfonyl or imino group, an oxygen or sulfur atom or a group corresponding to formula (5):

$$Z\text{-}(CH_2\text{—}Y\text{—}CH_2\text{-}Z')_o \qquad (5)$$

in which

Y is a direct bond, a $CH_2$ or CHOH group,

Z and Z' independently of one another represent an oxygen atom, an $NR^7$ group, where $R^7$ is hydrogen, a $C_{1-4}$ alkyl or a hydroxy-$C_{1-4}$-alkyl group, the group —O—$(CH_2)_p$—NH or NH—$(CH_2)_{p'}$—O, where p and p'=2 or 3, and o is a number of 1 to 4, such as for example 4,4'-diaminostilbene, 4,4'-diaminostilbene-2,2'-disulfonic acid monosodium or disodium salt, 4,4'-diaminodiphenyl methane, -sulfide, -sulfoxide, -amine, 4,4'-diaminodiphenylamine-2-sulfonic acid, 4,4'-diaminobenzophenone, -diphenyl ether, 3,3',4,4'-tetraminodiphenyl, 3,3'4,4'-tetraminobenzophenone, 1,3-bis-(2,4-diaminophenoxy)-propane, 1,8-bis-(2,5-diaminophenoxy)-3,6-dioxaoctane, 1,3-bis-(4-aminophenylamino)-propane, -2-propanol, 1,3-bis-[N-(4-aminophenyl)-2-hydroxyethylamino]-2-propanol, N,N-bis-[2-(4-aminophenoxy)-ethyl]-methylamine, N-phenyl-1,4-phenylenediamine.

The compounds mentioned above may be used both in free form and in the form of their physiologically compatible salts, more especially as salts of inorganic acids, such as hydrochloric acid or sulfuric acid.

Suitable phenols are, for example, 2-, 3- or 4-methoxyphenol, 3-dimethylaminophenol, 2-(2'-hydroxyethyl)- and 3,4-methylenedioxyphenol, resorcinol and 2-, 4- and 5-methylresorcinol, 2- and 4-chlororesorcinol, 2,5-dimethylresorcinol, pyrocatechol, hydroquinone, pyrogallol, phloroglucinol, hydroxyhydroquinone, 2,4- or 3,4-dihydroxybenzoic or phenylacetic acid, gallic acid, 2,4,6-trihydroxybenzoic acid or 2,4,5-trihydroxyacetophenone, 1-naphthol, 1,5-, 2,3- and 2,7-dihydroxynaphthalene, 6-dimethylamino-4-hydroxy-2-naphthalenesulfonic acid or 3,6-dihydroxy-2,7-naphthalenedisulfonic acid.

Suitable nitrogen-containing heterocyclic compounds are, for example, 2-, 3-, 4-amino-, 2-amino-3-hydroxy-, 2,6-diamino-, 2,5-diamino-, 2,3-diamino-, 2-dimethylamino-5-amino-, 2-methylamino-3-amino-6-methoxy-, 2,3-diamino-6-methoxy-, 2,6-dimethoxy-3,5-diamino-, 2,4,5-triamino- and 2,6-dihydroxy-3,4-dimethylpyridine, 2,4-dihydroxy-5,6-diamino-, 4,5,6-triamino-, 4-hydroxy-2,5,6-triamino-, 2-hydroxy-4,5,6-triamino-, 2,4,5,6-tetraamino-, 2-methylamino-4,5,6-triamino-, 2,4-, 4,5-diamino-, 2-amino-4-methoxy-6-methylpyrimidine, 3-amino-, 3-amino-5-hydroxy- and 3,5-diaminopyrazole, 2-, 3-, 8-aminoquinoline, 4-aminoquinaldine, 2-, 6-aminonicotinic acid, 5-aminoisoquinoline, 5-, 6-aminoindazole, 5- and 7-aminobenzimidazole and -benzothiazole, 2,5-dihydroxy-4-morpholinoaniline and indole and indoline derivatives, such as 4-, 5-, 6- and 7-aminoindole, 5,6-dihydroxyindole, 5,6-dihydroxyindoline and 4-hydroxyindoline. The compounds mentioned above may be used both in free form and in the form of their physiologically compatible salts, for example as salts of inorganic acids, such as hydrochloric acid or sulfuric acid.

These coloring systems may be further strengthened by suitable nitrogen-containing heterocycles such as, for example, piperidine, piperidine-2-, -3- or -4-carboxylic acid, pyridine, 2-, 3- or 4-hydroxypyridine, imidazole, 1-methylimidazole, histidine, pyrrolidine, pyrrolidone, pyrrolidone-5-carboxylic acid, pyrazole, 1,2,4-triazole, piperazine and physiologically compatible salts thereof.

Several dye precursors of the reactive compound (b) type may be simultaneously present in the colorant preparations according to the invention. Similarly, several benzo[b]furan-3-one and/or benzo[b]thiophen-3-one derivatives may also be present in the compositions according to the invention. Several of the other compounds from the group of amino acids, peptides, aromatic amines, aminophenols, phenols and nitrogen-containing heterocycles may also be present together should this be necessary for obtaining the required shade.

The benzo[b]furan-3-one and/or benzo[b]thiophen-3-one derivatives are present in the compositions according to the invention in quantities of preferably 0.02 to 8% by weight, more preferably 0.05 to 5% by weight and most preferably 0.1 to 2% by weight, based on the composition as a whole. The reactive compounds (b) are present in the compositions according to the invention in quantities of preferably 0.02 to 8% by weight, more preferably 0.05 to 5% by weight and most preferably 0.1 to 2% by weight, based on the composition as a whole.

In another embodiment, however, the color-changing compositions according to the invention may also contain other dyes and/or dye precursors.

The present invention is not limited in any way in regard to the dye precursors suitable for use in the compositions according to the invention. The compositions according to the invention may contain as dye precursors oxidation dye precursors of the primary and secondary intermediate type and precursors of "nature-analogous" dyes, such as indole and indoline derivatives and mixtures of representatives of these groups.

The primary intermediates used are normally primary aromatic amines containing another free or substituted hydroxy or amino group in the para- or ortho-position, diaminopyridine derivatives, heterocyclic hydrazones, 4-aminopyrazole derivatives and 2,4,5,6-tetraminopyrimidine and derivatives thereof.

According to the invention, it can be preferable to use a p-phenylenediamine derivative or a physiologically compatible salt thereof as primary intermediate. Particularly preferred p-phenylenediamine derivatives correspond to formula (6):

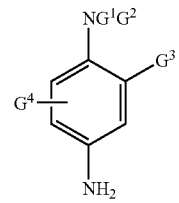

(6)

in which $G^1$ stands for a hydrogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical, a 4'-aminophenyl radical or a $C_{1-4}$ alkyl radical substituted by a nitrogen-containing group, a phenyl group or a 4'-aminophenyl group;

$G^2$ stands for a hydrogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical or a $C_{1-4}$ alkyl radical substituted by a nitrogen-containing group;

$G^3$ stands for a hydrogen atom, a halogen atom, such as a chlorine, bromine, iodine or fluorine atom, a $C_{1-4}$ alkyl radical, a $C_{1-4}$ monohydroxyalkyl radical, a $C_{1-4}$ hydroxyalkoxy radical, a $C_{1-4}$ acetylaminoalkoxy radical, a $C_{1-4}$ mesylaminoalkoxy radical or a $C_{1-4}$ carbamoylaminoalkoxy radical;

$G^4$ is a hydrogen atom, a halogen atom or a $C_{1-4}$ alkyl radical or if $G^3$ and $G^4$ are in the ortho position to one another, they may together form a bridging α,ω-alkylenedioxo group such as, for example, an ethylenedioxy group.

Examples of the $C_{1-4}$ alkyl radicals mentioned as substituents in the compounds according to the invention are the methyl, ethyl, propyl, isopropyl and butyl groups. Ethyl and methyl radicals are preferred alkyl radicals. According to the invention, preferred $C_{1-4}$ alkoxy radicals are, for example, methoxy or ethoxy radicals. Other preferred examples of a $C_{1-4}$ hydroxyalkyl group are a hydroxymethyl, a 2-hydroxyethyl, a 3-hydroxypropyl or a 4-hydroxybutyl group. A 2-hydroxyalkyl group is particularly preferred. According to the invention, examples of a halogen atom are the F, Cl or Br atom. A Cl atom is most particularly preferred. According to the invention, the other terms used are derived from the definitions given here. Examples of nitrogen-containing groups corresponding to formula (6) are, in particular, the amino groups, $C_{1-4}$ monoalkylamino groups, $C_{1-4}$ dialkylamino groups, $C_{1-4}$ trialkylammonium groups, $C_{14}$ monohydroxyalkylamino groups, imidazolinium and ammonium.

Particularly preferred p-phenylenediamines corresponding to formula (6) are selected from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(β-hydroxyethyl)-p-phenylenediamine, 4-N,N-bis-(β-hydroxyethyl)-amino-2-methylaniline, 4-N,N-bis-(β-hydroxyethyl)-amino-2-chloroaniline, 2-(β-hydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl- β-hydroxyethyl)-p-phenylene-diamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane and physiologically compatible salts thereof.

According to the invention, most particularly preferred p-phenylenediamine derivatives corresponding to formula (6) are p-phenylenediamine, p-toluylenediamine, 2-(β-hydroxyethyl)-p-phenylene-diamine and N,N-bis-(β-hydroxyethyl)-p-phenylenediamine In another preferred embodiment of the invention, compounds containing at least two aromatic nuclei substituted by amino and/or hydroxyl groups may be used as primary intermediates.

The binuclear primary intermediates which may be used in the coloring compositions according to the invention include in particular compounds corresponding to formula (7) and physiologically compatible salts thereof:

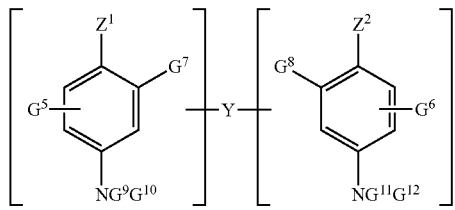

(7)

in which

Z$^1$ and Z$^2$ independently of one another stand for a hydroxyl or NH$_2$ radical which is optionally substituted by a C$_{1-4}$ alkyl radical, by a C$_{1-4}$ hydroxyalkyl radical and/or by a bridging group Y or which is optionally part of a bridging ring system, the bridging group Y is a C$_{1-14}$ alkylene group such as, for example, a linear or branched alkylene chain or an alkylene ring which may be interrupted or terminated by one or more nitrogen-containing groups and/or one or more hetero atoms, such as oxygen, sulfur or nitrogen atoms, and may optionally be substituted by one or more hydroxyl or C$_{1-8}$ alkoxy radicals, G$^5$ and G$^6$ independently of one another stand for a hydrogen or halogen atom, a C$_{1-4}$ alkyl radical, a C$_{1-4}$ monohydroxyalkyl radical, a C$_{2-4}$ polyhydroxyalkyl radical, a C$_{1-4}$ aminoalkyl radical or a direct bond to the bridging group Y, G$^7$, G$^8$, G$^9$, G$^{10}$, G$^{11}$ and G$^{12}$ independently of one another stand for a hydrogen atom, a direct bond to the bridging group Y or a C$_{1-4}$ alkyl radical, with the proviso that the compounds of formula (7) contain only one bridging group Y per molecule.

According to the invention, the substituents used in formula (7) are as defined in the foregoing.

Preferred binuclear primary intermediates corresponding to formula (7) are, in particular, N,N'-bis-(β-hydroxyethyl)-N,N'-bis-(4'-aminophenyl)-1,3-diaminopropanol, N,N'-bis-(β-hydroxyethyl)-N,N'-bis-(4'-aminophenyl)-ethylenediamine, N,N'-bis-(4-aminophenyl)-tetramethylene diamine, N,N'-bis-(β-hydroxyethyl)-N,N'-bis-(4'-aminophenyl)-tetramethylene diamine, N,N'-bis-(4-methylaminophenyl)-tetramethylene diamine, N,N'-bis-(ethyl)-N,N'-bis-(4'-amino-3'-methylphenyl)-ethylene diamine, 1,8-bis-(2,5-diaminophenoxy)-3,5-dioxaoctane, bis-(2-hydroxy-5-aminophenyl)-methane, 1,4-bis-(4-aminophenyl)-diazacycloheptane and 1,10-bis-(2,5-diaminophenyl)-1,4,7,10-tetraoxadecane and physiologically compatible salts thereof.

Most particularly preferred binuclear primary intermediates corresponding to formula (7) are N,N'-bis-(β-hydroxyethyl)-N,N'-bis-(4'-aminophenyl)-1,3-diaminopropanol, bis-(2-hydroxy-5-aminophenyl)-methane, N,N'-bis-(4-aminophenyl)-1,4-diazacycloheptane and 1,10-bis-(2,5-diaminophenyl)-1,4,7,10-tetraoxadecane or one of their physiologically compatible salts.

In another preferred embodiment of the invention, a p-aminophenol derivative or a physiologically compatible salt thereof is used as primary intermediate. Particularly preferred p-aminophenol derivatives correspond to formula (8):

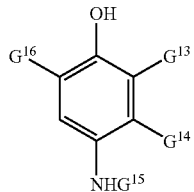

(8)

in which

G$^{13}$ stands for a hydrogen atom, a halogen atom, a C$_{1-4}$ alkyl radical, a C$_{1-4}$ monohydroxyalkyl radical, a (C$_{1-4}$)-alkoxy-(C$_{1-4}$)-alkyl radical, a C$_{1-4}$ aminoalkyl radical, a hydroxy-(C$_{1-4}$)-alkylamino radical, a C$_{1-4}$ hydroxyalkyloxy radical, a C$_{1-4}$ hydroxyalkyl-(C$_{1-4}$)-aminoalkyl radical or a (di-C$_{1-4}$-alkylamino)-(C$_{1-4}$)-alkyl radical, G$^{14}$ stands for a hydrogen atom or a halogen atom, a C$_{1-4}$ alkyl radical, a C$_{1-4}$ monohydroxyalkyl radical, a C$_{2-4}$ polyhydroxyalkyl radical, a (C$_{1-4}$)-alkoxy-(C$_{1-4}$)-alkyl radical, a C$_{1-4}$ aminoalkyl radical or a C$_{1-4}$ cyanoalkyl radical, G$^{15}$ stands for hydrogen, a C$_{1-4}$ alkyl radical, a C$_{1-4}$ monohydroxyalkyl radical, a C$_{2-4}$ polyhydroxyalkyl radical, a phenyl radical or a benzyl radical and G$^{16}$ stands for hydrogen or a halogen atom.

According to the invention, the substituents used in formula (8) are defined as in the foregoing.

Preferred p-aminophenols corresponding to formula (8) are, in particular, p-aminophenol, N-methyl-p-aminophenol, 4-amino-3-fluorophenol, 2-hydroxymethylamino-4-aminophenol, 4-amino-3-hydroxymethylphenol, 4-amino-2-(2-hydroxyethoxy)-phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)-phenol, 4-amino-2-fluorophenol, 4-amino-2-chlorophenol, 2,6-dichloro-4-aminophenol, 4-amino-2-((diethylamino)methyl)phenol and physiologically compatible salts thereof.

Most particularly preferred compounds corresponding to formula (8) are p-aminophenol, 4-amino-3-methylphenol, 4-amino-2-aminomethylphenol and 4-amino-2-((diethylamino)methyl)phenol.

The primary intermediate may also be selected from o-aminophenol and its derivatives such as, for example, 2-amino-4-methylphenol or 2-amino-4-chlorophenol.

In addition, the primary intermediate may be selected from heterocyclic primary intermediates such as, for example, the pyridine, pyrimidine, pyrazole, pyrazole/pyrimidine derivatives and physiologically compatible salts thereof.

Preferred pyridine derivatives are, in particular, the compounds described in GB 1,026,978 and GB 1,153,196, such as 2,5-diaminopridine, 2-(4-methoxyphenyl)-amino-3-aminopyridine, 2,3-diamino-6-methoxypyridine, 2-(β-methoxyethyl)-amino-3-amino-6-methoxypyridine and 3,4-diaminopyridine.

Preferred pyrimidine derivatives are, in particular, the compounds described in DE 2359399, JP 02019576 A2 and WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyridine.

Preferred pyrazole derivatives are, in particular, the compounds described in DE 3843892, DE 4133957, WO 94/08969, WO 94/08970, EP 740931 and DE 19543988, such as 4,5-diamino-1-methylpyrazole, 4,5-diamino-1-(β-hydroxyethyl)-pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert.butyl-1-methylpyrazole, 4,5-diamino-1-tert.butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)-amino-1-methylpyrazole.

Preferred pyrazole-pyrimidine derivatives are, in particular, the derivatives of pyrazole-[1,5-a]-pyrimidine corresponding to formula (9) below and tautomeric forms thereof where a tautomeric equilibrium exists:

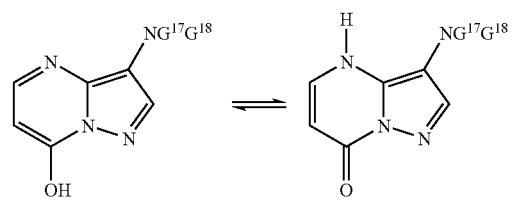

(9)

in which

G$^{17}$, G$^{18}$, G$^{19}$ and G$^{20}$ independently of one another stand for a hydrogen atom, a $C_{1-4}$ alkyl radical, an aryl radical, a $C_{1-4}$ hydroxyalkyl radical, a $C_{2-4}$ polyhydroxyalkyl radical, a $(C_{1-4})$-alkoxy-$(C_{1-4})$-alkyl radical, a $C_{1-4}$ aminoalkyl radical which may optionally be protected by an acetylureide or sulfonyl radical, a $(C_{1-4})$-alkylamino-$(C_{1-4})$-alkyl radical, a di[$(C_{1-4})$-alkyl]-$(C_{1-4})$-aminoalkyl radical, the dialkyl radicals optionally forming a carbon cycle or a heterocycle with 5 or 6 links, a $C_{1-4}$ hydroxyalkyl or a di-$(C_{1-4})$-[hydroxyalkyl]-$(C_{1-4})$-aminoalkyl radical;

the X radicals independently of one another stand for a hydrogen atom, a $C_{1-4}$ alkyl radical, an aryl radical, a $C_{1-4}$ hydroxyalkyl radical, a $C_{2-4}$ polyhydroxyalkyl radical, a $C_{1-4}$ aminoalkyl radical, a $(C_{1-4})$-alkylamino-$(C_{1-4})$-alkyl radical, a di[$(C_{1-4})$-alkyl]-$(C_{1-4})$-aminoalkyl radical, the dialkyl radicals optionally forming a carbon cycle or a heterocycle with 5 or 6 links, a $C_{1-4}$ hydroxyalkyl or a di-$(C_{1-4})$-[hydroxyalkyl]-$(C_{1-4})$-aminoalkyl radical, an amino radical, a $C_{1-4}$ alkyl or a di-$(C_{1-4}$ hydroxyalkyl)-amino radical, a halogen atom, a carboxylic acid group or a sulfonic acid group, i has the value 0, 1, 2 or 3, p has the value 0 or 1, q has the value 0 or 1 and n has the value 0 or 1, with the proviso that the sum of p+q is not 0, where p+q=2, n has the value 0 and the groups NG$^{17}$G$^{18}$ and NG$^{19}$G$^{20}$ occupy the (2,3); (5,6); (6,7); (3,5) or (3,7) positions;

where p+q=1, n has the value 1 and the groups NG$^{17}$G$^{18}$ (or NG$^{19}$G$^{20}$) and the group OH occupy the (2,3); (5,6); (6,7); (3,5) or (3,7) positions.

The substituents used in formula (9) are as defined in the foregoing.

If the pyrazole-[1,5-a]-pyrimidine corresponding to formula (9) above contains a hydroxy group in one of the positions 2, 5 or 7 of the ring system, a tautomeric equilibrium exists as illustrated, for example, in the following scheme:

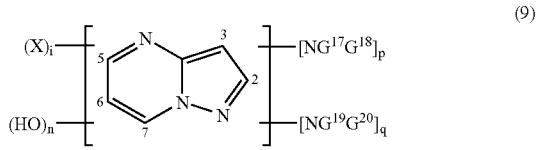

Among the pyrazole-[1,5-a]-pyrimidines corresponding to formula (9) above, the following may be particularly mentioned:

pyrazole-[1,5-a]-pyrimidine-3,7-diamine;
2,5-dimethylpyrazole-[1,5-a]-pyrimidine-3,7-diamine;
pyrazole-[1,5-a]-pyrimidine-3,5-diamine;
2,7-dimethylpyrazole-[1,5-a]-pyrimidine-3,5-diamine;
3-aminopyrazole-[1,5-a]-pyrimidin-7-ol;
3-aminopyrazole-[1,5-a]-pyrimidin-5-ol;
2-(3-aminopyrazole-[1,5-a]-pyrimidin-7-ylamino)-ethanol;
2-(7-aminopyrazole-[1,5-a]-pyrimidin-3-ylamino)-ethanol;
2-[(3-aminopyrazole-[1,5-a]-pyrimidin-7-yl)-(2-hydroxyethyl)-amino]-ethanol;
2-[(7-aminopyrazole-[1,5-a]-pyrimidin-3-yl)-(2-hydroxyethyl)-amino]-ethanol;
5,6-dimethylpyrazole-[1,5-a]-pyrimidine-3,7-diamine;
2,6-dimethylpyrazole-[1,5-a]-pyrimidine-3,7-diamine;
2,5,N7,N7-tetramethylpyrazole-[1,5-a]-pyrimidine-3,7-diamine;

and physiologically compatible salts thereof and tautomeric forms thereof where a tautomeric equilibrium exists.

The pyrazole-[1,5-a]-pyrimidines corresponding to formula (9) above may be prepared by cyclization from an aminopyrazole or from hydrazine, as described in the literature.

The secondary intermediates used are generally m-phenylenediamine derivatives, naphthols, resorciol and resorcinol derivatives, pyrazolones and m-aminophenol derivatives. Particularly suitable secondary intermediates are 1-naphthol, 1,5-, 2,7- and 1,7-dihydroxynaphthalene, 5-amino-2-methylphenol, m-aminophenol, resorcinol, resorcinol monomethylether, m-phenylenediamine, 1-phenyl-3-methyl-5-pyrazolone, 2,4-dichloro-3-aminophenol, 1,3-bis-(2,4-diaminophenoxy)-propane, 2-chloreresorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

According to the invention, preferred secondary intermediates are:

m-aminophenol and derivatives thereof such as, for example, 5-amino-2-methylphenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-(ethylamino)-4-methylphenol and 2,4-dichloro-3-aminophenol, o-aminophenol and derivatives thereof, m-diaminobenzene and derivatives thereof such as, for example, 2,4-diaminophenoxyethanol, 1,3-bis-(2,4-diaminophenoxy)-propane, 1-methoxy-2-amino-4-(2'-hydroxyethylamino)-benzene, 1,3-bis-(2,4-diaminophenyl)-propane, 2,6-bis-(2-hydroxyethylamino)-1-methylbenzene and 1-amino-3-bis-(2'-hydroxyethyl)-aminobenzene, o-diaminobenzene and derivatives thereof such as, for example, 3,4-diaminobenzoic acid and 2,3-diamino-1-methylbenzene, di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihdroxynaphthalene, 1,7-dihydroxynaphthalene, 1,8-dihdroxynaphthalene, 2,7-dihdroxynaphthalene and 2,3-dihdroxynaphthalene, morpholine derivatives such as, for example, 6-hydroxybenzomorpholine and 6-aminobenzomorpholine, quinoxaline derivatives such as, for example, 6-methyl-1,2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxyindole, pyrimidine derivatives such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or methylenedioxybenzene derivatives such as, for example, 1-hydroxy-3,4-methylenedioxybenzene, 1-amino-3,4-methylenedioxybenzene and 1-(2'-hydroxyethyl)-amino-3,4-methylenedioxybenzene.

Particularly preferred secondary intermediates are, for example, 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methyl resorcinol, 5-methyl resorcinol, 2,5-dimethyl resorcinol and 2,6-dihydroxy-3,4-dimethylpyridine.

The oxidation dye precursors or the substantive dyes do not have to be single compounds. On the contrary, other components may be present in small quantities in the hair colorants according to the invention due to the processes used to produce the individual dyes providing these other components do not adversely affect the coloring result or have to be ruled out for other reasons, for example toxicological reasons.

So far as the dyes suitable for use in the hair colorants and tinting compositions according to the invention are concerned, reference is also expressly made to the work by Ch. Zviak, The Science of Hair Care, Chapter 7 (pages 248–250; substantive dyes) and Chapter 8, pages 264–267; oxidation dye precursors), published as Volume 7 of the Series "Dermatology" (Ed.: Ch. Culnan and H. Maibach), Marcel Dekker Inc., New York/Basel, 1986, and to the "Europäische Inventar der Kosmetik-Rohstoffe" published by the Europäische Gemeinschaft and available on floppy disk from the Bundesverband Deutscher Industrie- und Handelsunternehmen für Arzneimittel, Reformwaren und Körperpflegemittel d.V., Mannheim.

The oxidation dye precursors are present in the compositions according to the invention in quantities of preferably 0.01 to 20% by weight and more preferably 0.5 to 5% by weight, based on the composition as a whole.

In a preferred embodiment of the invention, the reactive compounds are stored separately from the benzo[b]furan-3-one and/or benzo[b]thiophen-3-one derivatives and the oxidation dyes so that these components do not react prematurely. Thus, these compounds may be stored in separate aqueous media, such as emulsions for example, which are only combined immediately before application to the fibers.

In addition, one or more of the components may be formulated as one or more aqueous media and the other component(s) may be formulated as powders. In this embodiment, the powder-form components are added to the aqueous medium immediately before use. In a preferred embodiment of the invention, the component containing the compounds of formula (1) may be formulated as a powder.

In addition, a premature reaction can also be avoided by formulating the components together as a powder-form hair color. The components are only activated just before application to the fibers by addition of an aqueous component.

Finally, the components may be separately dispersed in an inert medium, for example an inert oil.

In a preferred embodiment of the invention, the separately formulated components may be applied successively, optionally after the addition of water, in which case intermediate rinsing may optionally be carried out after application of the first component.

Preferred precursors of "nature-analogous" dyes are indoles and indolines which contain at least one hydroxy or amino group, preferably as a substituent on the six ring. These groups may carry further substituents, for example in the form of an etherification or esterification of the hydroxy group or an alkylation of the amino group.

Particularly suitable precursors of "nature-analogous" hair dyes are derivatives of 5,6-dihydroxyindoline corresponding to formula (10a):

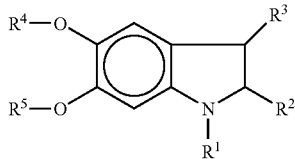

in which—independently of one another—
R$^1$ is hydrogen, a C$_{1-4}$ alkyl group or a C$_{1-4}$ hydroxyalkyl group,
R$^2$ is hydrogen or a —COOH group, the —COOH group optionally being present as a salt with a physiologically compatible cation,
R$^3$ is hydrogen or a C$_{1-4}$ alkyl group,
R$^4$ is hydrogen, a C$_{1-4}$ alkyl group or a group —CO—R$^6$, where R$^6$ is a C$_{1-4}$ alkyl group, and
R$^5$ is one of the groups mentioned for R$^4$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis is placed on N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

Other particularly suitable precursors of "nature-analogous" hair dyes are derivatives of 5,6-dihydroxyindole corresponding to formula (10b):

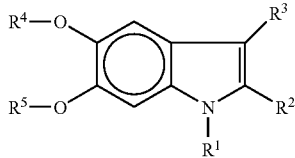

in which—independently of one another—
R$^1$ is hydrogen, a C$_{1-4}$ alkyl group or a C$_{1-4}$ hydroxyalkyl group,
R$^2$ is hydrogen or a —COOH group, the —COOH group optionally being present as a salt with a physiologically compatible cation,
R$^3$ is hydrogen or a C$_{1-4}$ alkyl group,
R$^4$ is hydrogen, a C$_{1-4}$ alkyl group or a group —CO—R$^6$, where R$^6$ is a C$_{1-4}$ alkyl group, and
R$^5$ is one of the groups mentioned for R$^4$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, particular emphasis is placed on N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives may be used both as free bases and in the form of their physiologically compatible salts with inorganic or organic acids, for example hydrochlorides, sulfates and hydrobromides, in the colorants according to the invention. The indole or indoline derivatives are present in these colorants in quantities of normally 0.05 to 10% by weight and preferably 0.2 to 5% by weight.

Where dye precursors of the indoline or indole type in particular are used, it has been found to be of advantage to use an amino acid and/or an oligopeptide as alkalizing agent.

Besides the dye precursors, the compositions according to the invention may contain substantive dyes for further modifying the shades. Substantive dyes are typically selected from nitrophenylenediamines, nitroaminophenols, azo dyes, anthraquinones or indophenols. Preferred substantive dyes are the compounds known under the International names or commercial names of HC Yellow 2, HC Yellow 4, HC Yellow 5, HC Yellow 6, Basic Yellow 57, HC Orange 1, Disperse Orange 3, HC Red 1, HC Red 3, HC Red 13, HC Red BN, Basic Red 76, HC Blue 2, HC Blue 12, Disperse Blue 3, Basic Blue 7, Basic Blue 26, Basic Blue 99, HC Violet 1, Disperse Violet 1, Disperse Violet 4, Basic Violet 14, Acid Violet 43, Disperse Black 9, Acid Black 52, Basic Brown 16 and Basic Brown 17 and also 1,4-bis-(β-hydroxyethyl)-amino-2-nitrobenzene, 3-nitro-4-(β-hydroxyethyl)-aminophenol, 4-amino-2-nitrodiphenylamine-2'-carboxylic acid, 6-nitro-1,2,3,4-tetrahydroquinoxaline, 2-hydroxy-1,4-naphthoquinone, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene. The colorants according to the invention in this embodiment preferably contain the substantive dyes in a quantity of 0.01 to 20% by weight, based on the colorant as a whole.

The preparations according to the invention may also contain naturally occurring dyes such as, for example, henna red, henna neutral, henna black, camomile blossom, sandalwood, black tea, black alder bark, sage, logwood, madder root, catechu, sedre and alkanet.

The preparations according to the invention contain the components essential to the invention preferably in a suitable aqueous, alcoholic or aqueous/alcoholic carrier. For coloring hair, such carriers are, for example, creams, emulsions, gels or even surfactant-containing foaming solutions such as, for example, shampoos, foam aerosols or other preparations suitable for application to the hair. However, these compounds may even be integrated into a powder-form or tablet-form formulation.

Aqueous/alcoholic solutions in the context of the invention are aqueous solutions containing 3 to 70% by weight of a C$_{1-4}$ alcohol, more particularly ethanol or isopropanol. The compositions according to the invention may additionally contain other organic solvents such as, for example, methoxybutanol, benzyl alcohol, ethyl diglycol or 1,2-propylene glycol. Water-soluble organic solvents are preferred.

In principle, the color can be oxidatively developed with atmospheric oxygen. However, a chemical oxidizing agent is preferably used, particularly when human hair is to be not only colored, but also lightened. Particularly suitable oxidizing agents are persulfates, chlorites and, in particular, hydrogen peroxide or addition products thereof with urea, melamine or sodium borate. Oxidation may also be carried out with enzymes. In this case, the enzymes may be used both to produce oxidizing per compounds and to enhance the effect of an oxidizing agent present in small quantities. Thus, the enzymes (enzyme class 1: oxidoreductases) can transfer electrons from suitable primary intermediates (reducing agents) to atmospheric oxygen. Oxidases, such as tyrosinase, ascorbate oxidase and laccase, are preferred for this purpose, as are glucoseoxidase, uricase or pyruvate oxidase. Mention is also made of the procedure whereby the effect of small quantities (for example 1% and less, based on the formulation as a whole) of hydrogen peroxide is enhanced by peroxidases.

One advantage of the coloring system according to the invention is its stability to the oxidizing agents typically used in oxidative hair coloring. Thus, the hair coloring system according to the invention may be used not only as sole coloring component, but also, for example, for shading or for improving the fastness properties of oxidative colorants. In this embodiment, the composition preferably contains an oxidizing agent. According to the invention, hydrogen peroxide is particularly preferred.

If the colorant is not a one-component product, it is preferably prepared immediately before application by mixing the preparations containing the dye precursors and optionally the preparation of the oxidizing agent. The ready-to-use hair coloring preparation should preferably have a pH of 6 to 12. In a particularly preferred embodiment, the hair colorant is applied in a weakly alkaline medium.

The application temperatures may be in the range from 15 to 40° C. After a contact time of about 5 to 45 minutes, the hair colorant is removed from the hair to be colored by rinsing. There is no need for the hair to be washed with a shampoo where a carrier of high surfactant content, for example a coloring shampoo, has been used.

The compositions according to the invention may also contain any of the known active substances, additives and auxiliaries typical of such preparations. In many cases, the compositions contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the preparations according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps),
ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16,
acyl sarcosides containing 10 to 18 carbon atoms in the acyl group,
acyl taurides containing 10 to 18 carbon atoms in the acyl group,
acyl isethionates containing 10 to 18 carbon atoms in the acyl group,
sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups,
linear alkane sulfonates containing 12 to 18 carbon atoms,
linear α-olefin sulfonates containing 12 to 18 carbon atoms,
α-sulfofatty acid methyl esters of fatty acids containing 12 to 18 carbon atoms,
alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids containing 12 to 24 carbon atoms and 1 to 6 double bonds according to DE-A-39 26 344,
esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated C$_{8-22}$ carboxylic acids, such as oleic acid, stearic acid, isostearic acid and palmitic acid.

Nonionic surfactants contain, for example, a polyol group, a poly-alkylene glycol ether group or a combination of polyol and polyglycol ether groups as the hydrophilic group. Examples of such compounds are products of the addition of 2 to 30 mol ethylene oxide and/or 0 to 5 mol propylene oxide onto linear fatty alcohols containing 8 to 22 carbon atoms, onto fatty acids containing 12 to 22 carbon atoms and onto alkylphenols containing 8 to 15 carbon atoms in the alkyl group,
C$_{12-22}$ fatty acid monoesters and diesters of products of the addition of 1 to 30 mol ethylene oxide onto glycerol,
C$_{8-22}$ alkyl mono- and oligoglycosides and ethoxylated analogs thereof and
products of the addition of 5 to 60 mol ethylene oxide onto castor oil and hydrogenated castor oil.

Preferred nonionic surfactants are alkyl polyglycosides corresponding to the general formula R$^1$O-(Z)$_x$. These compounds are characterized by the following parameters.

The alkyl group R$^1$ contains 6 to 22 carbon atoms and may be both linear and branched. Primary linear and 2-methyl-branched aliphatic groups are preferred. Such alkyl groups are, for example, 1-octyl, 1-decyl, 1-lauryl, 1-myristyl, 1-cetyl and 1-stearyl. 1-Octyl, 1-decyl, 1-lauryl and 1-myristyl are particularly preferred. Where so-called "oxo alcohols" are used as starting materials, compounds with an odd number of carbon atoms in the alkyl chain predominate.

The alkyl polyglyosides suitable for use in accordance with the invention may, for example, contain only one particular alkyl group R$^1$. However, such compounds are normally prepared from natural fats and oils or mineral oils. In this case, mixtures corresponding to the starting compounds or corresponding to the particular working up of these compounds are present as the alkyl groups R.

Particularly preferred alkyl polyglycosides are those in which R$^1$ consists
essentially of C$_8$ and C$_{10}$ alkyl groups,
essentially of C$_{12}$ and C$_{14}$ alkyl groups, essentially of $C_8$ to $C_{16}$ alkyl groups or
essentially of $C_{12}$ to $C_{16}$ alkyl groups.

Any mono- or oligosaccharides may be used as the sugar unit Z. Sugars containing 5 or 6 carbon atoms and the corresponding oligosaccharides are normally used. Examples of such sugars are glucose, fructose, galactose, arabinose, ribose, xylose, lyxose, allose, altrose, mannose, gulose, idose, talose and sucrose. Preferred sugar units are glucose, fructose, galactose, arabinose and sucrose; glucose is particularly preferred.

The alkyl polyglycosides suitable for use in accordance with the invention contain on average 1.1 to 5 sugar units. Alkyl polyglycosides with x values of 1.1 to 1.6 are preferred. Alkyl glycosides where x is 1.1 to 1.4 are most particularly preferred.

Besides acting as surfactants, the alkyl glycosides may also be used to improve the fixing of perfume components to the hair. Accordingly, in cases where the effect of the perfume oil on the hair is intended to last longer than the duration of the hair treatment, alkyl glycosides will preferably be used as another ingredient of the preparations according to the invention.

Alkoxylated homologs of the alkyl polyglycosides mentioned may also be used in accordance with the invention. These homologs may contain on average up to 10 ethylene oxide and/or propylene oxide units per alkyl glycoside unit.

Zwitterionic surfactants may also be used, particularly as co-surfactants. In the context of the invention, zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Also suitable, particularly as co-surfactants, are ampholytic surfactants. Ampholytic surfactants are surface-active compounds which, in addition to a $C_{8-18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

According to the invention, the cationic surfactants used are particularly those of the quaternary ammonium compound, esterquat and amidoamine type.

Preferred quaternary ammonium compounds are ammonium halides, more particularly chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride and the imidazolium compounds known under the INCI names of Quaternium-27 and Quaternium-83. The long alkyl chains of the above-mentioned surfactants preferably contain 10 to 18 carbon atoms.

Esterquats are known substances which contain both at least one ester function and at least one quaternary ammonium group as structural element. Preferred esterquats are quaternized ester salts of fatty acids with triethanolamine, quaternized ester salts of fatty acids with diethanol alkylamines and quaternized ester salts of fatty acids with 1,2-dihydroxypropyl dialkylamines. Such products are marketed, for example, under the names of Stepantex®, Dehyquart® and Armocare®. The products Armocare® VGH-70, an N,N-bis-(2-palmitoyloxyethyl)-dimethyl ammonium chloride, and Dehyquart® F-75 and Dehyquart® AU-35 are examples of such esterquats.

The alkyl amidoamines are normally prepared by amidation of natural or synthetic fatty acids and fatty acid cuts with dialkyl aminoamines. A compound from this group particularly suitable for the purposes of the invention is the stearamidopropyl dimethylamine obtainable under the name of Tegoamid® S 18.

Other cationic surfactants suitable for use in accordance with the invention are the quaternized protein hydrolyzates.

Also suitable for the purposes of the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

One example of a quaternary sugar derivative suitable for use as a cationic surfactant is the commercially available product Glucquat® 100 (INCI name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

The preparations according to the invention preferably may also contain a conditioning agent selected from the group consisting of cationic surfactants, cationic polymers, alkyl amidoamines, paraffin oils, vegetable oils and synthetic oils.

Cationic polymers can be preferred conditioning agents. These are generally polymers containing a quaternary nitrogen atom, for example in the form of an ammonium group. The following are examples of preferred cationic polymers:

Quaternized cellulose derivatives commercially available under the names of Celquat® and Polymer JR®. The compounds Celquat® H 100, Celquat® L 200 and Polymer JR®400 are preferred quaternized cellulose derivatives.

Polymeric dimethyl diallyl ammonium salts and copolymers thereof with acrylic acid and with esters and amides of acrylic acid and methacrylic acid. The products commercially available under the names of Merquat®100 (poly(dimethyl diallyl ammonium chloride)), Merquat®550 (dimethyl diallyl ammonium chloride/acrylamide copolymer) and Merquat® 280 (dimethyl diallyl ammonium chloride/acrylic acid copolymer) are examples of such cationic polymers.

Copolymers of vinyl pyrrolidone with quaternized derivatives of dialkylaminoacrylate and methacrylate, such as vinyl pyrrolidone/dimethylaminomethacrylate copolymers quaternized, for example, with diethyl sulfate. Compounds such as these are commercially available under the names of Gafquat®734 and Gafquat®755.

Copolymers of vinyl pyrrolidone with methoimidazolinium chloride which are commercially available under the name of Luviquat®.

Quaternized polyvinyl alcohol.

The polymers with quaternary nitrogen atoms in the main polymer chain known by the names of Polyquaternium 2, Polyquaternium 17, Polyquaternium 18 and Polyquaternium 27.

Cationic polymers from the first four groups mentioned are particularly preferred, Polyquaternium 2, Polyquaternium 10 and Polyquaternium 22 being most particularly preferred.

Other suitable conditioning agents are silicone oils, more particularly dialkyl and alkylaryl siloxanes, such as for example dimethyl polysiloxane and methylphenyl polysiloxane, and alkoxylated and quaternized analogs thereof. Examples of such silicones are the products marketed by Dow Corning under the names of DC 190, DC 200, DC 344, DC 345 and DC 1401 and the products Q2-7224 (manufacturer: Dow Corning; a stabilized trimethyl silyl amodimethicone), Dow Corning® 929 Emulsion (containing a hydroxylamino-modified silicone which is also known as amodimethicone), SM-2059 (manufacturer: General Electric), SLM-55067 (manufacturer: Wacker) and Abil® Quat 3270 and 3272 (manufacturer: Th. Goldschmidt; diquaternary polydimethyl siloxanes, Quaternium-80).

Other suitable conditioning agents are paraffin oils, synthetically produced oligomeric alkenes and vegetable oils, such as jojoba oil, sunflower oil, orange oil, almond oil, wheatgerm oil and peach kernel oil.

Phospholipids, for example soya lecithin, egg lecithin and kephalins, are also suitable hair-conditioning compounds.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, zwitterionic and amphoteric polymers such as, for example, acrylamidopropyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as maleic acid and lactic acid, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solvents and solubilizers, such as ethanol, isopropanol, ethylene glycol, propylene glycol, glycerol and diethylene glycol, fiber-structure-improving agents, more particularly mono-, di- and oligosaccharides such as, for example, glucose, galactose, fructose and lactose, quaternized amines, such as methyl-1-alkylamidoethyl-2-alkylimidazolinium methosulfate, defoamers, such as silicones, dyes for coloring the preparation, antidandruff agents, such as piroctone olamine, zinc omadine and climbazol, UV filters, more particularly derivatized benzophenones, cinnamic acid derivatives and triazines, substances for adjusting the pH value, for example typical acids, more particularly food-grade acids and acidic amino acids and also bases and alkaline amino acids, active substances, such as allantoin, pyrrolidone carboxylic acids and salts thereof and bisabolol, vitamins, provitamins and vitamin precursors, more particularly those of groups A, $B_3$, $B_5$, C, E, F and H, plant extracts, such as the extracts of green tea, oak bark, stinging nettle, hamamelis, hops, camomile, burdock root, horse willow, hawthorn, lime blossom, almond, aloe vera, pine needle, horse chestnut, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, ginseng and ginger root, cholesterol, consistency factors, such as sugar esters, polyol esters or polyol alkyl ethers, fats and waxes, such as spermaceti, beeswax, montan wax and paraffins, fatty acid alkanolamides, complexing agents, such as EDTA, NTA, β-alanine diacetic acid and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, styrene/PVP and styrene/acrylamide copolymers, pearlizers, such as ethylene glycol mono- and distearate and PEG-3-distearate, pigments,
stabilizers for hydrogen peroxide and other oxidizing agents,
propellents, such as propane/butane mixtures, $N_2O$, dimethyl ether, $CO_2$ and air,
antioxidants.

Information on other optional components and the quantities in which they are used can be found in the reference books known to the expert, for example Kh. Schrader, Grundlagen und Rezepturen der Kosmetika, 2nd Edition, Hüthig Buch Verlag, Heidelberg, 1989.

In a second embodiment, the present invention relates to a process for coloring keratin fibers in which a composition according to the invention is applied to the fibers and, after a contact time, is rinsed off again.

In a third embodiment, the present invention relates to the use of the compositions according to the invention for coloring keratin fibers.

The following Examples are intended to illustrate the invention.

EXAMPLES

1 Synthesis of the 3-hydroxy-5-oxybenzo[b]thiophenes (tautomers of the 5-oxybenzo[b]thiophen-3-ones)

1.1 Synthesis of 3,5-dihydroxybenzo[b]thiophene (I)

This compound was prepared in accordance with A. Pawlik, Dissertation, Tech. Universität Braunschweig 1995, 98–101.

1.2 Synthesis of 5-carboxymethoxy-3-hydroxybenzo[b]thiophene

This molecule was prepared to synthesis scheme 1:

1.2.1 Synthesis of 5-hydroxy-2-mercaptobenzoic acid (II)

This compound was prepared in accordance with A. Pawlik, Dissertation, Tech. Universität Braunschweig 1995, 98–101.

1.2.2 Synthesis of 5-hydryoxy-2-butoxycarbonylmethylsulfanyl benzoic acid butyl ester (III)

83.40 g (490 mmol) II, 196.00 g (4.90 mol) NaOH and 102.13 g (735 mmol) bromoacetic acid were heated under reflux for 32 h in 1.5 l MeOH and 600 ml water. The pH was then adjusted to pH 1 with concentrated HCl before the solvent was removed in vacuo. The residue was heated for 12 h on a water separator with 1.5 l n-butanol and 15 ml concentrated $H_2SO_4$. After removal of the solvent, the residue was taken up in 1 l chloroform, washed once with water and dried over $Na_2SO_4$. The solvent was removed. After the residue had been dissolved in ethylacetate, 101.80 g (299 mmol, 61%) III were obtained by precipitation with n-pentane.

1.2.3 Synthesis of 5-methoxymethyloxy-2-butoxycarbonylmethylsulfanyl benzoic acid butyl ester (IV)

Under an extraction thimble filled with 3 A molecular sieve, 1.70 g (5 mmol) III, 2.21 ml (25 mmol) dimethoxymethane and a spatula tip of p-toluenesulfonic acid were heated under reflux for 72 h in 75 ml dichloromethane. Subsequent column filtration (50 g $SiO_2$, n-hexane:ethyl acetate=5:1) gave 1.61 g (4.2 mmol, 84%) IV.

1.2.4 Synthesis of 2-butoxycarbonyl-3-hydroxy-5-methoxymethyloxybenzo[b]thiophene (V)

6.20 g (16 mmol) IV and 0.80 g (20 mmol, 60%) NaH were stirred for 5 h at room temperature in 80 ml DMF. The Synthesis scheme 1: preparation of 5-carboxymethoxy-3-hydroxybenzo[b]thiophene

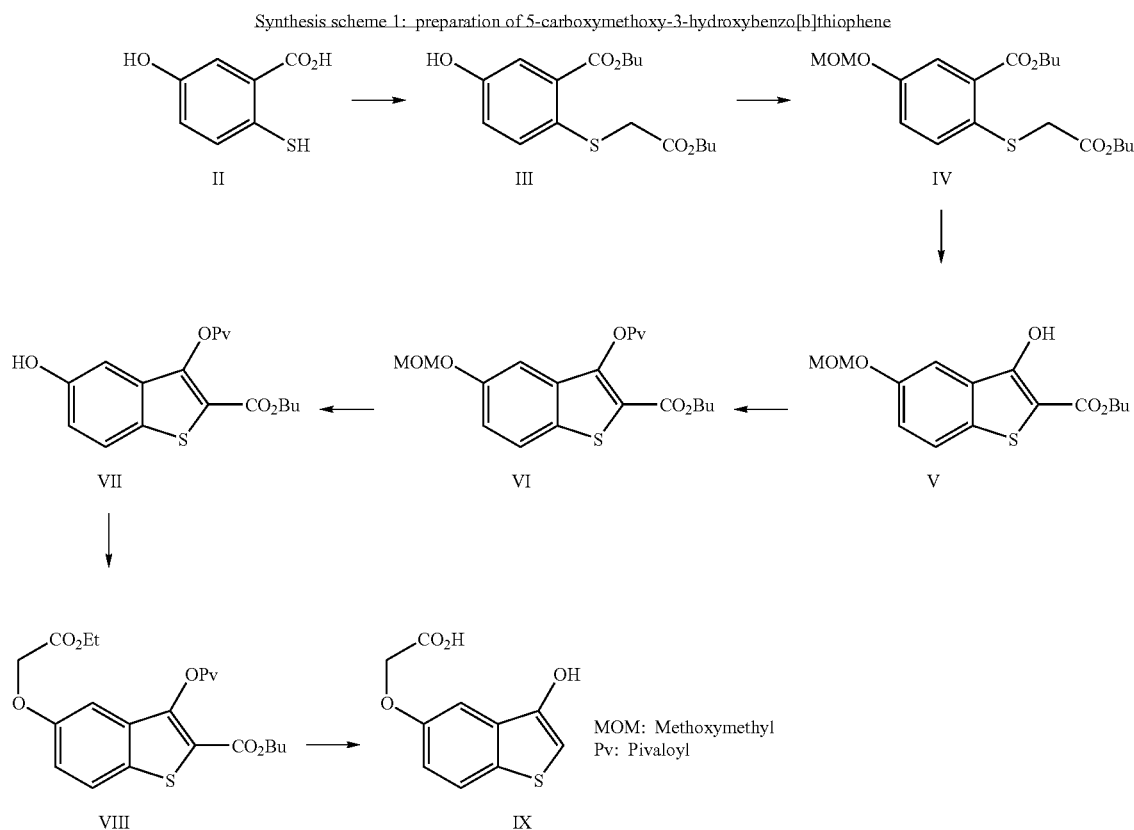

MOM: Methoxymethyl
Pv: Pivaloyl solvent was removed and the residue was taken up in 250 ml CHCl₃, washed three times with water and dried over Na₂SO₄. Recrystallization from n-hexane gave 4.22 g (13.6 mmol, 85%) V.

1.2.5 Synthesis of 2-butoxycarbonyl-5-methoxymethyloxy-3-pivaloyloxybenzo[b]thiophene (VI)

6.21 g (20 mmol) V and 3.70 ml (30 mmol) pivaloyl chloride were stirred for 12 h at room temperature in 150 ml pyridine. After removal of the solvent, flash chromatography (200 g SiO₂ n-hexane:ethyl acetate=5:1+1% acetic acid, applied with CHCl₃) produced 7.39 g (18.7 mmol), 94%) VI.

1.2.6 Synthesis of 2-butoxycarbonyl-5-hydroxy-3-pivaloyloxybenzo[b]thiophene (VII)

A few drops of concentrated HCl were added to 5.92 g (15 mmol) VI in 150 ml acetic acid, followed by stirring for 10 h at room temperature. 500 ml water were then added to the reaction solution, followed by repeated extraction with Et₂O. The combined organic phases were dried over Na₂SO₄ and freed from the solvent. Recrystallization from diethyl-ether:n-hexane=4:1 produced 4.21 g (12 mmol, 80%) VII.

1.2.7 Synthesis of 2-butoxycarbonyl-5-ethoxycarbonyl-methoxy-3-pivaloyloxybenzo[b]thiophene (VIII)

3.50 g (10 mmol) VII, 2.22 ml (20 mmol) bromoacetic acid ethyl ester and 2.48 g (25 mmol) K₂CO₃ were heated under reflux for 5 h in 250 ml acetone. The reaction mixture was filtered. The filtrate was freed from the solvent. After recrystallization from n-hexane, VIII was obtained in a yield of 4.00 g (9.2 mmol, 92%).

1.2.8 Synthesis of 5-carboxymethoxy-3-hydroxybenzo[b]thiophene (IX)

1.96 g (4.5 mmol) VIII and 2.70 g (67.5 mmol) NaOH were heated under reflux for 15 h in 300 ml degassed water. The pH was then adjusted to pH 1 with concentrated HCl and the aqueous phase was extracted three times with ethyl acetate. The combined organic phases were dried over Na₂SO₄. Flash chromatography (200 g SiO₂, ethyl acetate: acetic acid=100:1, pre-adsorption: 10 g SiO₂/ethanol) yielded 801 mg (3.6 mmol, 79%) IX.

2 Synthesis of the 5,6-dioxy-3-hydroxybenzo[b]thiophene derivatives (tautomers of 5,6-dioxybenzo[b]thiophen-3-one derivatives)

The 5,6-dioxy-3-hydroxybenzo[b]thiophene derivatives were prepared to synthesis scheme 2.

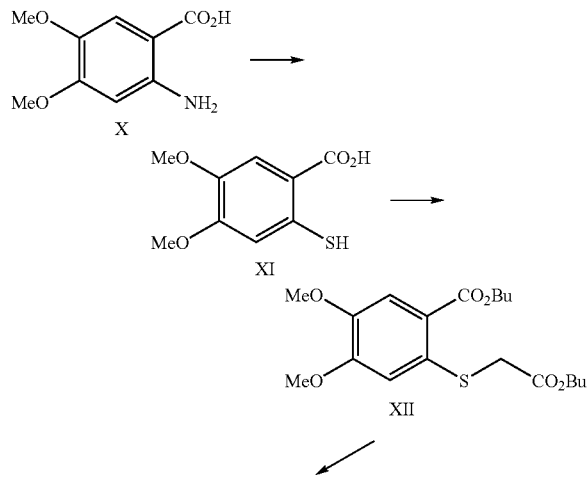

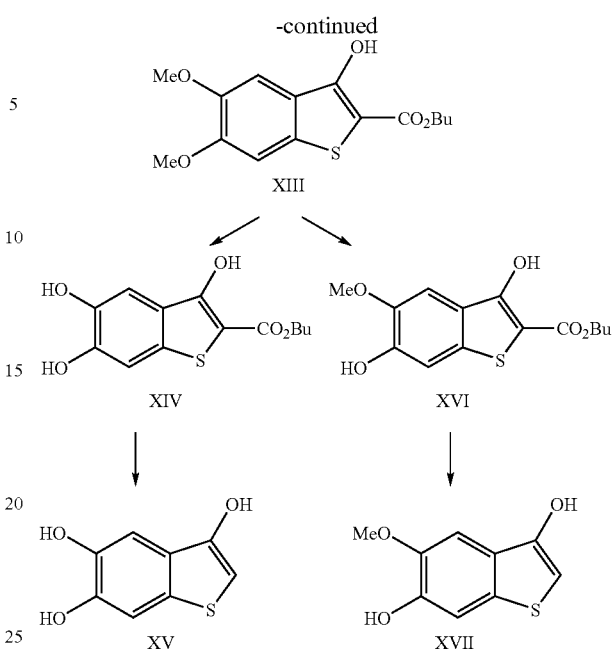

2.1 Synthesis of 3,5,6-trihydroxybenzo[b]thiophene (XV)

2.1.1 Synthesis of 4,5-dimethoxy-2-mercaptobenzoic acid (XI)

This compound was prepared in accordance with J. Szabò et al., Acta Chim. Acad. Sci. Hung. 1958, 17, 201–209.

2.1.2 Synthesis of 4,5-dimethoxy-2-butoxycarbonylmethyl-sulfanyl benzoic acid butyl ester (XII)

2.36 g (11 mmol) XI, 2.29 g (17 mmol) bromoacetic acid and 4.40 g (110 mmol) NaOH were stirred under reflux for 24 h in a solution of 50 ml MeOH and 25 ml water. After acidification with concentrated HCl to pH 1, the solvents were removed in vacuo and the residue was heated for another 60 h on a water separator with 50 ml n-butanol and 2 ml concentrated H₂SO₄.

The reaction mixture was freed from the solvent and the residue was taken up in 100 ml CHCl₃. After the organic phase had been washed with water and dried over Na₂SO₄, flash chromatography (100 g SiO₂, n-hexane:ethyl acetate=10:1+1% acetic acid) yielded 3.80 g (9.9 mmol, 90%) XII.

2.1.3 Synthesis of 2-butoxycarbonyl-5,6-dimethoxy-3-hydroxybenzo[b]thiophene (XIII)

19.22 g (50 mmol) XII were stirred for 3.5 h at room temperature with 2.75 g (63 mmol), 60% NaH in 250 ml DMF. The mixture was then hydrolyzed with 50 ml saturated NH₄Cl solution and the solvent was removed. The residue was taken up in 500 ml CHCl₃, filtered, washed with water and dried over Na₂SO₄. Flash chromatography (250 g SiO₂, n-hexane:ethyl acetate=5:1+1% acetic acid) gave 14.70 g (47 mmol, 95%) XIII.

2.1.4. Synthesis of 2-butoxycarbonyl-3,5,6-trihydroxybenzo[b]thiophene (XIV)

2.79 g (9.0 mmol) XIII in 150 ml CH₂Cl₂ were stirred with 2.64 ml (27 mmol) BBr₃ for 2 h at 0° C. After hydrolysis with 75 ml water, the product was extracted with ethyl acetate. The combined organic phases were dried over Na₂SO₄ and, after flash chromatography (200 g SiO₂, n-hexane:ethyl acetate=2:1+1% acetic acid), XIV was obtained in a yield of 2.48 g (8.8 mmol, 98%).

2.1.5 Synthesis of 3,5,6-trihydroxybenzo[b]thiophene (XV)

2.82 g (10 mmol) XIV and 6.00 g (150 mmol) NaOH were heated under reflux for 3.5 h in 300 ml degassed water. The still hot solution was then acidified with concentrated HCl to pH 1. The compound XV precipitating on cooling in an ice bath was removed and washed with a little diethylether. A yield of 1.57 g XV (8.6 mmol, 86%) was obtained.

2.2 Synthesis of 5-methoxy-3,6-dihydroxybenzo[b]thiophene (XVII)

2.2.1 Synthesis of 2-butoxycarbonyl-3,6-dihydroxy-5-methoxybenzo[b]thiophene (XVI)

4.45 ml (60 mmol) ethanethiol and 2.62 g (60 mmol, 60%) NaH were stirred for 15 mins. at room temperature in 100 ml DMF. 9.31 g (30 mmol) XIII were added to the resulting solution, followed by refluxing for 4 h. After hydrolysis with 25 ml saturated $NH_4Cl$ solution, the solvents were removed in vacuo, the residue was taken up in 500 ml ethyl acetate and washed with water. After drying over $Na_2SO_4$, flash chromatography (250 g $SiO_2$, n-hexane:ethyl acetate=2:1+1% acetic acid), pre-adsorption: 25 g $SiO_2$/ $CHCl_3$) yielded 6.89 g (23 mmol, 78%) XVI.

2.2.2 Synthesis of 3,6-dihydroxy-5-methoxybenzo[b]thiophene (XVII)

2.96 g (10 mmol) XVI and 6.00 g NaOH were heated under reflux for 3.5 h in 100 ml degassed water. The still hot solution was then acidified with concentrated HCl to pH 1. The compound XVII precipitating on cooling in an ice bath was removed and washed with a little n-hexane. A yield of 1.23 g XVII (6.3 mmol, 63%) was obtained.

By extraction of the aqueous filtrate with ethyl acetate and subsequent flash chromatography (50 g $SiO_2$, n-hexane: ethyl acetate=2:1+1% acetic acid, pre-adsorption: 2 g $SiO_2$/ ethyl acetate), the yield of XVII was increased to a total of 1.73 g (8.8 mmol, 88%).

3 Synthesis of 5-oxybenzo[b]furan-3-one derivatives

The 5-oxybenzo[b]furan-3-one derivatives were prepared to synthesis scheme 3:

3.2 Synthesis of 5-carboxymethoxybenzo[b]furan-3-one (XX)

3.2.1 Synthesis of 5-ethoxycarbonylmethoxybenzo[b]furan-3-one (XIX)

3.00 g (20 mmol) XVIII, 3.96 g (40 mmol) $K_2CO_3$ and 5.54 ml (50 mmol) bromoacetic acid ethyl ester were heated under reflux for 72 h in 150 ml tetrahydrofuran. After filtration, the solvent was removed. Flash chromatography (200 g $SiO_2$, n-hexane:ethyl acetate=2:1) produced 4.63 g (19.6 mmol, 98%) XIX.

3.2.2 Synthesis of 5-carboxymethoxybenzo[b]furan-3-one (XX)

4.72 g (20 mmol) XIX were heated under reflux for 15 h in a mixture of 200 ml tetrahydrofuran, 100 ml water and 10 ml concentrated $H_2SO_4$. Ethyl acetate and saturated NaCl solution were added to the reaction solution. The phases were separated and the aqueous phase was extracted three times with ethyl acetate. The combined organic phases were dried over $Na_2SO_4$ and freed from the solvent. Flash chromatography (200 g $SiO_2$, n-hexane:ethyl acetate=1:2+1% acetic acid, applied with ethanol) produced 2.78 g (13 mmol, 67%) XX.

3.3 Synthesis of 5-(2'-hydroxyethoxy)-benzo[b]furan-3-one (XXIII)

3.3.1 Synthesis of 5-hydroxy-3-methoxybenzo[b]furan (XXI)

900 mg (6.0 mmol) XVIII, 788 μl (7.2 mmol) orthoformic acid trimethyl ester and 57 mg (0.3 mmol) p-toluenesulfonic aid monohydrate were heated under reflux for 12 h in 70 ml methanol. The reaction was stopped by addition of saturated $NaHCO_3$ solution and the solvent was removed. Subsequent flash chromatography (100 g $SiO_2$, n-hexane:ethyl acetate=2:1, applied with ethanol) yielded 717 mg (4.4 mmol, 73%) XXI.

3.3.2 Synthesis of 3-methoxy-5-(2'-acetoxyethoxy)-benzo[b]furan (XXII)

164 mg (1.0 mmol) XXI and 48 mg (1.2 mmol, 60%) NaH were stirred for 30 mins. in 20 ml DMF at 0° C. 227 μl (2.0 mmol, 97%) 2-bromoethyl acetate were added to the result-

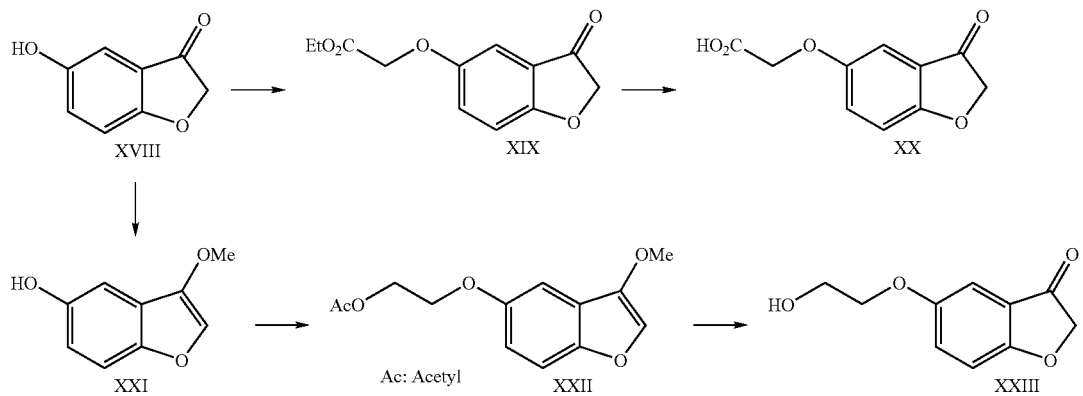

Synthesis scheme 3: preparation of 5-oxybenzo[b]furan-3-one derivatives.

3.1 Synthesis of 5-hydroxybenzo[b]furan-3-one (XVIII)

The 5-hydroxybenzo[b]furan-3-one (XVIII) was synthesized by the procedure described by M. C. Kloetzel et al. in J. Org. Chem. 1955, 20, 38–49.

ing suspension which was then stirred for 72 h at room temperature. The reaction was quenched by addition of 3 ml saturated $NH_4Cl$ solution and the solvents were removed in vacuo. The residue was taken up in ethyl acetate and water, the aqueous phase was extracted twice with ethyl acetate and the combined organic phases were dried over $Na_2SO_4$. After column filtration (40 g $SiO_2$, n-hexane:ethyl acetate=2:1, applied with ethyl acetate), XXII was obtained in a yield of 220 mg (0.88 mmol, 88%).

3.3.3 Synthesis of 5-(2'-hydroxyethoxy)-benzo[b]furan-3-one (XXIII)

751 mg (7.0 mmol) XXII were stirred under reflux for 12 h in a mixture of 40 ml tetrahydrofuran, 20 ml water and 0.5 ml conc. $H_2SO_4$. Ethyl acetate and saturated NaCl solution were added to the reaction mixture cooled to room temperature. After separation of the phases, the aqueous phase was extracted twice with ethyl acetate and the combined organic phases were dried over $Na_2SO_4$. After column filtration (50 g $SiO_2$, n-hexane:ethyl acetate=1:1+1% acetic acid, applied with ethyl acetate), XXIII was obtained in a yield of 448 mg (2.3 mmol, 77%).

4 Application Examples

All quantities are understood to be percentages by weight unless otherwise stated.

The following abbreviations are used:
1 5-hydroxybenzo[b]thiophen-3-one (I)
2 5-carboxymethoxybenzo[b]thiophen-3-one (IX)
3 5,6-dihydroxybenzo[b]thiophen-3-one (XV)
4 6-hydroxy-5-methoxybenzo[b]thiophen-3-one (XVII)
5 3-carboxymethoxybenzo[b]furan-3-one (XX)
6 5-hydroxybenzo[b]furan-3-one (XVIII)
7 5-(2'-hydroxyethoxy)-benzo[b]furan-3-one (XXIII)
A 4-N,N-dimethylaminobenzaldehyde
B 4-N,N-dimethylaminocinnamaldehyde
C vanillin
D 4-N,N-dimethylamino-1-naphthaldehyde
E isatin 4.1 Test Series A First, quantities of 0.1 g of dyes 1 to 7 were mixed with the corresponding equimolar quantity of carbonyl compounds A to E, 0.1 g Natrosol® HR250[1] and 0.05 g ammonium sulfate and, after addition of 9 g water, the pH was adjusted to 10 with a 25% ammonia solution. This swelling was then made up with water to 10 g.

[1] hydroxyethyl cellulose (INCI name: Hydroxyethylcellulose) (Hercules)

Immediately before application, these solutions were mixed with water in a ratio of 1:1 for the reaction without hydrogen peroxide. In the case of the reaction with hydrogen peroxide, the solutions were correspondingly mixed in a ratio of 1:1 with a 3% aqueous hydrogen peroxide solution (commercial product Poly Color Tönungswäsche).

Hair tresses (Alkinco Virgin White, 0.5 g) were placed in 10 g of the resulting preparations for 10 minutes, rinsed with water and dried.

The coloring results are set out in Table I.

TABLE I

| Compound No. | Carbonyl compound | Shade Without $H_2O_2$ | Shade With $H_2O_2$ |
|---|---|---|---|
| 1 | A | High red | Red |
| 1 | B | Violet-brown | Violet-brown |
| 1 | C | Gold-yellow | Gray-green |
| 1 | D | Brown-orange | Gray-orange |
| 1 | E | Red-orange | Orange |
| 2 | A | Orange-red | Red-orange |
| 2 | B | Light brown | Light brown |
| 2 | C | Light orange | Yellow-gray |
| 2 | D | Gray-red | Pale red |

TABLE I-continued

| Compound No. | Carbonyl compound | Shade Without $H_2O_2$ | Shade With $H_2O_2$ |
|---|---|---|---|
| 3 | A | Dark orange | Dark orange |
| 3 | B | Red-orange | Red-orange |
| 3 | C | Orange-yellow | Olive-yellow |
| 3 | D | Orange | Gray-yellow |
| 4 | A | Orange | Orange |
| 4 | B | Gray-orange | Gray-orange |
| 4 | C | Yellow | Olive |
| 4 | D | Light orange | Olive |
| 5 | A | Light orange | Light orange |
| 5 | B | Orange | Orange |
| 5 | C | Light yellow | Gray-orange |
| 5 | D | Light orange | Pale orange |
| 6 | A | Red-orange | Orange |
| 6 | B | Red | Orange-red |
| 6 | C | Orange-yellow | Yellow |
| 6 | D | Orange | Light orange |
| 7 | A | Red-orange | Orange |
| 7 | B | Red | Orange-red |
| 7 | C | Yellow | Pastel yellow |
| 7 | D | Orange | Light orange |

4.2 Test Series B

First, quantities of 0.1 g of dyes 1, 4, 6 and 7 and equimolar quantities of carbonyl compounds A to D as shown in Table II were mixed with 0.1 g Natrosol® HR250[1] and 0.05 g ammonium sulfate and, after addition 9 g water, the pH was adjusted to 10 with a 25% ammonia solution. This swelling was then made up with water to 10 g.

5 g of this coloring mixture were mixed with 5 g of a preparation containing the other raw materials identified in Table II. Immediately before application, the solutions were mixed in a ratio of 1:1 with a 3% aqueous hydrogen peroxide solution (commercial product Poly Color Tönungswäsche).

The resulting preparation was applied to a hair tress (Alkinco Virgin White) in a ratio by weight of 4:1. The contact time was 30 mins. The tress was then rinsed with water and dried.

The coloring results are set out in Table II.

TABLE II

| Raw material | Formulation No/Quantity % by wt. | | | |
|---|---|---|---|---|
| | 1 | 2 | 3 | 4 |
| $C_{12-18}$ Fatty alcohol mixture | 5.75 | 5.75 | 5.75 | 5.75 |
| Eumulgin ® B2[2] | 0.5 | 0.5 | 0.5 | 0.5 |
| Texapon ® NSO[3] | 6.25 | 6.25 | 6.25 | 6.25 |
| Polymer ® JR[4] | 0.4 | 0.4 | 0.4 | 0.4 |
| Sodium sulfite | 0.15 | 0.15 | 0.15 | 0.15 |
| Ammonium sulfate | 0.25 | 0.25 | 0.25 | 0.25 |
| Natrosol ® 250 HR | 0.5 | 0.5 | 0.5 | 0.5 |
| 2,4,5,6-Tetraaminopyrimidine sulfate | — | — | 0.76 | — |
| p-Toluylenediamine sulfate | 0.164 | — | 0.092 | — |
| p-Phenylenediamine dihydrochloride | — | 0.092 | — | 0.08 |
| 3-Methyl-4-aminophenol | 0.015 | 0.017 | 0.012 | 0.01 |
| 2-Aminomethyl-4-aminophenol dihydrochloride | — | — | 0.021 | 0.01 |
| Resorcinol | 0.061 | 0.038 | 0.36 | — |
| 2-Methylresorcinol | 0.014 | — | 0.22 | — |
| 3-Aminophenol | 0.008 | 0.0034 | 0.004 | — |
| 2,7-Dihydroxynaphthalene | 0.004 | — | 0.28 | — |
| 2-Methylamino-3-amino-6-methoxypyridine | 0.007 | — | — | — |

TABLE II-continued

| Raw material | Formulation No/Quantity % by wt. | | | |
|---|---|---|---|---|
| | 1 | 2 | 3 | 4 |
| 2-Amino-3-hydroxypyridine | 0.001 | — | — | 0.026 |
| 1,3-Bis-(2',4'-diaminophenoxy)-propane tetrahydrochloride | — | 0.0005 | — | — |
| 5-Amino-2-methylphenol | — | — | — | 0.030 |
| A | 0.52 | — | — | — |
| B | — | 0.48 | — | — |
| C | — | — | 0.55 | — |
| D | — | — | — | 0.55 |
| 1 | 0.5 | — | — | — |
| 4 | — | 0.5 | — | — |
| 6 | — | — | 0.5 | — |
| 7 | — | — | — | 0.5 |
| Water | to 100 | to 100 | to 100 | to 100 |

[2] ethoxylated cetylstearyl alcohol containing ca. 20 EO units (INCI name: Ceteareth-20) (Cognis)
[3] lauryl ether sulfate sodium salt (INCI name: Sodium Laureth Sulfate, ca. 28% active substance) (Cognis)
[4] quaternized hydroxyethyl cellulose (INCI name: Polyquaternium-10) (Amerchol)

TABLE III

| Formulation No. | Color |
|---|---|
| 1 | Brown-orange |
| 2 | Light brown |
| 3 | Orange-red |
| 4 | Light brown |

4.3 Test Series C

Test Procedure.

15 mmol 3,5-dihydroxybenzo[b]thiophene (Table VI) or 15 mmol 5-hydroxybenzo[b]furan-3-one (Table V) and 15 mmol of the carbonyl compounds mentioned in Table IV or Table V were separately dissolved in 100 g of a 1% by weight Natrosol® 250 HR swelling additionally containing 0.5% by weight ammonium sulfate.

For coloring without hydrogen peroxide, 2.5 g of the particular swellings containing the two components were mixed together immediately before coloring.

For coloring with hydrogen peroxide, 2.5 g of a 3% primary intermediate preparation (Poly Color Tönungswäsche) were added to 1.25 g of the particular swellings of the two components.

In both cases, the pH was then adjusted with tartaric acid or ammonia solution (25%) as indicated in Table IV or Table V.

Coloring was carried out with quantities of 5 g of the ready-to-use formulations on wool swatches (measuring 4×3 cm) of the ISO105/F Code (application temperature 32° C., contact time 30 mins.). After rinsing and drying, the following results were obtained (color codes of the Taschenlexikon der Farben, 1975 Edition, Musterschmidt-Verlag, Zürich, Göttingen)

TABLE IV

Coloring results with 3,5-dihydroxybenzo[b]thiophene (I)

| | Coloring result | | |
|---|---|---|---|
| | Without $H_2O_2$ | | With $H_2O_2$ |
| Carbonyl compounds | pH 10 | pH 6 | pH 10 |
| Anthracene-9-aldehyde | Gray-yellow | Gray-yellow | Yellow-gray |
| 4-Hydroxy-3-methoxycinnamaldehyde | Tomato red | English red | Olive-gray |
| Terephthalaldehyde | Gray-red | Gray-red | Gray-red |
| Isophthalaldehyde | Light orange | Carrot red | Pale yellow |
| 1-Methylindole-3-aldehyde | Copper | Gray-orange | Gray-orange |
| 4-Nitrobenzaldhyde | Brown red | Brown red | Pale orange |
| Indole-3-aldehyde | Gray-orange | Light orange | Gray-orange |
| 4-Formyl-1-methyl-quinolinium-p-toluenesulfonate | Gray-ruby | Gray-violet | Blue-green |
| 2-Formyl-1-methyl-quinolinium-p-toluenesulfonate | Violet-gray | Purple-gray | Nile green |

TABLE V

Coloring results with 5-hydroxybenzo[b]furan-3-one (XVIII)

| | Coloring result | | |
|---|---|---|---|
| | Without $H_2O_2$ | | With $H_2O_2$ |
| Carbonyl compounds | pH 10 | pH 6 | pH 10 |
| Anthracene-9-aldehyde | Light orange | Pale yellow | Light orange |
| 4-Hydroxy-3-methoxy-cinnamaldehyde | Brown yellow | Brown-orange | Ochre yellow |
| Terephthalaldehyde | Sun yellow | Cadmium yellow | Broom yellow |
| Isophthalaldehyde | Sulfur yellow | Naples yellow | Sun yellow |
| 1-Methylindole-3-aldehyde | Orange | Yellow-orange | Orange-yellow |
| 4-Nitrobenzaldhyde | Light yellow | Light yellow | Corn yellow |
| Indole-3-aldehyde | Light orange | Light yellow | Amber yellow |
| 4-Formyl-1-methyl-quinolinium-p-toluenesulfonate | Matt violet | Blue-gray | Brown-gray |
| 2-Formyl-1-methyl-quinolinium-p-toluenesulfonate | Gray-blue | Matt blue | Gray-green |

What is claimed is:

1. A dye precursor composition for coloring keratinous fibers comprising, in a cosmetically acceptable medium,
   (a) at least one compound selected from the group consisting of 5-carboxymethoxy-benzo[b]thiophen-3-one, 5,6-dihydroxybenzo[b]thiophen-3-one and 6-hydroxy-5-methoxybenzo[b]thiophen-3-one, 5-carboxymethoxybenzo[b]furan-3-one, and 5-(2'-hydroxyethoxy)-benzo[b]-furan-3-one; and
   (b) at least one reactive compound selected from the group consisting of
      (b1) reactive carbonyl compounds selected from the group of aromatic, heteroaromatic or unsaturated aldehydes or ketones, dialdehydes or diketones or acetals, semiaminals or imine derivatives of the reactive carbonyl compounds, and (b2) CH-active compounds corresponding to formula (2) or (3):

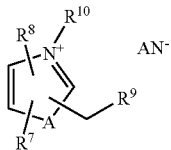
(2)

in which $R^{10}$ is a $C_{1-10}$ alkyl group, a $C_{2-4}$ alkenyl group, a $C_{2-4}$ hydroxyalkyl group, a $C_{2-4}$ carboxyalkyl group, a $C_{2-4}$ sulfoalkyl group or an aralkyl group, $R^7$ and $R^8$ independently of one another represent a hydrogen atom, a $C_{1-4}$ alkyl group, a halogen atom, a hydroxy group, a $C_{1-4}$ alkoxy group or a nitro group or together form a fused aromatic ring, $R^9$ is a hydrogen atom, a $C_{1-4}$ alkyl group or an aryl group, A is an oxygen or a sulfur atom, the group —CH=CH— or >N—$R^{11}$, where $R^{11}$ is a $C_{1-4}$ alkyl group, a $C_{2-4}$ carboxyalkyl group, a $C_{2-4}$ sulfoalkyl group, a $C_{2-4}$ sulfoxyalkyl group, a $C_{2-4}$ hydroxyalkyl group or an aralkyl group, and $AN^-$ is an anion selected from halide, $C_{1-4}$ alkyl sulfate, $C_{1-4}$ alkanesulfonate, arenesulfonate, $C_{1-4}$ perfluoroalkanesulfonate, tetrafluoroborate, perhalogenate, sulfate, hydrogen sulfate or carboxylate,

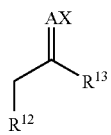
(3)

in which $R^{12}$ is a $C_{1-4}$ acyl group, a $C_{1-4}$ alkylsulfonyl group, a $C_{1-4}$alkylsulfinyl group, a $C_{1-4}$ alkylamino group, a di-$C_{1-4}$-alkyamino group, a vinyl carbonyl group, a methineimino group, a nitrile group, an ester or carboxylic acid amide group which may optionally be substituted by a $C_{1-4}$ alkyl group, a $C_{2-4}$ hydroxyalkyl group or an aryl group, and $R^{13}$ represents a $C_{1-4}$ acyl group, a $C_{1-4}$ alkoxy group, a $C_{1-4}$ alkylamino group, a $C_{1-4}$ acylamino group or a di-$C_{1-4}$-alkylamino group; the substituents $R^{12}$ and $R^{13}$ together with the rest of the molecule may also form a 5-, 6- or 7-membered ring system from the series of thiazolidine-2,5-diones, thiazolidine-2-thion-5-ones, perhydropyrimidine-2,4,6-triones, perhydropyrimidine-2-thione-4,6-diones, cyclopentane1,3diones, cyclohexane-1,3-diones, indane-1,3-diones, 2-pyrazoline-5-ones, 1,2-dihydro-6-hydroxy-2-hydroxypyridines or enol esters thereof, and AX represents oxygen, sulfur or a dicyanomethylene group.

2. The composition of claim 1 wherein the reactive carbonyl compound is isatin or a derivative thereof.

3. The composition of claim 2 wherein the reactive carbonyl compound is isatin.

4. The composition of claim 1 wherein the reactive carbonyl compound is an aromatic aldehyde or derivative thereof.

5. The composition of claim 4 wherein the reactive carbonyl compound is selected from the group consisting of 4-N,N-dimethylaminobenzaldehyde, 4-N,N-dimethylaminocinnamaldehyde, vanillin and 4-N,N-dimethylamino-1-naphthaldehyde.

6. The composition of claim 1 further comprising at least one oxidation dye precursor of the primary intermediate and/or secondary intermediate type.

7. The composition of claim 1 wherein the dye precursor is of the indole or indoline type.

8. The composition of claim 1 further comprising at least one substantive dye.

9. The composition of claim 1 further comprising an oxidizing agent.

10. The composition of claim 9 wherein the oxidizing agent is hydrogen peroxide.

11. A method for coloring keratinous fibers comprising applying the composition of claim 1 to the keratinous fibers and then rinsing it off the fibers.

* * * * *